United States Patent
Rowe

(10) Patent No.: US 8,285,010 B2
(45) Date of Patent: Oct. 9, 2012

(54) BIOMETRICS BASED ON LOCALLY CONSISTENT FEATURES

(75) Inventor: Robert K. Rowe, Corrales, NM (US)

(73) Assignee: Lumidigm, Inc., Albuquerque, NM (US)

( * ) Notice: Subject to any disclaimer, the term of this patent is extended or adjusted under 35 U.S.C. 154(b) by 1209 days.

(21) Appl. No.: 12/051,173

(22) Filed: Mar. 19, 2008

(65) Prior Publication Data

US 2008/0232653 A1 Sep. 25, 2008

Related U.S. Application Data

(60) Provisional application No. 60/896,063, filed on Mar. 21, 2007.

(51) Int. Cl.
*G06K 9/00* (2006.01)
(52) U.S. Cl. .......... 382/124; 382/115; 382/117
(58) Field of Classification Search .......... 382/115, 382/117, 124; 600/322, 316, 323
See application file for complete search history.

(56) References Cited

U.S. PATENT DOCUMENTS

| | | |
|---|---|---|
| 3,508,830 A | 4/1970 | Hopkins et al. |
| 3,619,060 A | 11/1971 | Johnson |
| 3,854,319 A | 12/1974 | Burroughs et al. |
| 3,872,443 A | 3/1975 | Ott |
| 3,910,701 A | 10/1975 | Henderson et al. |
| RE29,008 E | 10/1976 | Ott |
| 4,035,083 A | 7/1977 | Woodriff et al. |
| 4,142,797 A | 3/1979 | Astheimer |
| 4,169,676 A | 10/1979 | Kaiser |
| 4,170,987 A | 10/1979 | Anselmo et al. |
| 4,260,220 A | 4/1981 | Whitehead |
| 4,322,163 A | 3/1982 | Schiller |
| 4,427,889 A | 1/1984 | Muller |
| 4,537,484 A | 8/1985 | Fowler |
| 4,598,715 A | 7/1986 | Machler et al. |
| 4,653,880 A | 3/1987 | Sting et al. |
| 4,654,530 A | 3/1987 | Dybwad |
| 4,655,225 A | 4/1987 | Dahne et al. |
| 4,656,562 A | 4/1987 | Sugino |
| 4,657,397 A | 4/1987 | Oehler et al. |
| 4,661,706 A | 4/1987 | Messerschmidt et al. |
| 4,684,255 A | 8/1987 | Ford |

(Continued)

FOREIGN PATENT DOCUMENTS

CN 1307711 A 8/2001

(Continued)

OTHER PUBLICATIONS

Chinese Patent Application No. 2006/80038579.4, First Office Action mailed on Mar. 23, 2011, 7 pages.

(Continued)

*Primary Examiner* — Vu Le
*Assistant Examiner* — Aklilu Woldemariam
(74) *Attorney, Agent, or Firm* — Marsh Fischmann & Breyfogle LLP

(57) ABSTRACT

Systems, devices, methods, and software are described for biometric sensors that permit a reduction in the size of the sensing area without significant reduction in biometric functionality of the sensor. A skin site of an individual is illuminated, and light scattered from the skin site is received. An image of a locally consistent feature of the skin site is formed from the received light. The locally consistent feature is analyzed to perform a biometric function.

62 Claims, 16 Drawing Sheets

U.S. PATENT DOCUMENTS

| | | |
|---|---|---|
| 4,699,149 A | 10/1987 | Rice |
| 4,712,912 A | 12/1987 | Messerschmidt |
| 4,730,882 A | 3/1988 | Messerschmidt |
| 4,747,147 A | 5/1988 | Sparrow |
| 4,787,013 A | 11/1988 | Sugino et al. |
| 4,787,708 A | 11/1988 | Whitehead |
| 4,830,496 A | 5/1989 | Young |
| 4,853,542 A | 8/1989 | Milosevic et al. |
| 4,857,735 A | 8/1989 | Noller |
| 4,859,064 A | 8/1989 | Messerschmidt et al. |
| 4,866,644 A | 9/1989 | Shenk et al. |
| 4,867,557 A | 9/1989 | Takatani et al. |
| 4,882,492 A | 11/1989 | Schlager |
| 4,883,953 A | 11/1989 | Koashi et al. |
| 4,936,680 A | 6/1990 | Henkes et al. |
| 4,937,764 A | 6/1990 | Komatsu et al. |
| 4,944,021 A | 7/1990 | Hoshino et al. |
| 4,975,581 A | 12/1990 | Robinson et al. |
| 5,015,100 A | 5/1991 | Doyle |
| 5,019,715 A | 5/1991 | Sting et al. |
| 5,028,787 A | 7/1991 | Rosenthal et al. |
| 5,051,602 A | 9/1991 | Sting et al. |
| 5,055,658 A | 10/1991 | Cockburn |
| 5,068,536 A | 11/1991 | Rosenthal |
| 5,070,874 A | 12/1991 | Barnes et al. |
| 5,077,803 A | 12/1991 | Kato et al. |
| 5,088,817 A | 2/1992 | Igaki et al. |
| 5,109,428 A | 4/1992 | Igaki et al. |
| 5,146,102 A | 9/1992 | Higuchi et al. |
| 5,158,082 A | 10/1992 | Jones |
| 5,163,094 A | 11/1992 | Prokoski et al. |
| 5,177,802 A | 1/1993 | Fujimoto et al. |
| 5,178,142 A | 1/1993 | Harjunmaa et al. |
| 5,179,951 A | 1/1993 | Knudson |
| 5,204,532 A | 4/1993 | Rosenthal |
| 5,222,495 A | 6/1993 | Clarke et al. |
| 5,222,496 A | 6/1993 | Clarke et al. |
| 5,223,715 A | 6/1993 | Taylor |
| 5,225,678 A | 7/1993 | Messerschmidt |
| 5,230,702 A | 7/1993 | Lindsay et al. |
| 5,237,178 A | 8/1993 | Rosenthal et al. |
| 5,243,546 A | 9/1993 | Maggard |
| 5,257,086 A | 10/1993 | Fateley et al. |
| 5,258,922 A | 11/1993 | Grill |
| 5,267,152 A | 11/1993 | Yang et al. |
| 5,268,749 A | 12/1993 | Weber et al. |
| 5,291,560 A * | 3/1994 | Daugman ..................... 382/117 |
| 5,299,570 A | 4/1994 | Hatschek |
| 5,303,026 A | 4/1994 | Strobl et al. |
| 5,311,021 A | 5/1994 | Messerschmidt |
| 5,313,941 A | 5/1994 | Braig et al. |
| 5,321,265 A | 6/1994 | Block |
| 5,331,958 A | 7/1994 | Oppenheimer |
| 5,335,288 A | 8/1994 | Faulkner |
| 5,348,003 A | 9/1994 | Caro |
| 5,351,686 A | 10/1994 | Steuer et al. |
| 5,355,880 A | 10/1994 | Thomas et al. |
| 5,360,004 A | 11/1994 | Purdy et al. |
| 5,361,758 A | 11/1994 | Hall et al. |
| 5,366,903 A | 11/1994 | Lundsgaard et al. |
| 5,372,135 A | 12/1994 | Mendelson et al. |
| 5,379,764 A | 1/1995 | Barnes et al. |
| 5,402,778 A | 4/1995 | Chance |
| 5,405,315 A | 4/1995 | Khuri et al. |
| 5,413,096 A | 5/1995 | Hart |
| 5,413,098 A | 5/1995 | Benaron et al. |
| 5,419,321 A | 5/1995 | Evans |
| 5,435,309 A | 7/1995 | Thomas et al. |
| 5,441,053 A | 8/1995 | Lodder et al. |
| 5,452,723 A | 9/1995 | Wu et al. |
| 5,459,317 A | 10/1995 | Small et al. |
| 5,459,677 A | 10/1995 | Kowalski et al. |
| 5,460,177 A | 10/1995 | Purdy et al. |
| 5,483,335 A | 1/1996 | Tobias |
| 5,494,032 A | 2/1996 | Robinson et al. |
| 5,505,726 A | 4/1996 | Meserol |
| 5,507,723 A | 4/1996 | Keshaviah |
| 5,515,847 A | 5/1996 | Braig et al. |
| 5,518,623 A | 5/1996 | Keshaviah et al. |
| 5,523,054 A | 6/1996 | Switalski et al. |
| 5,533,509 A | 7/1996 | Koashi et al. |
| 5,537,208 A | 7/1996 | Bertram et al. |
| 5,539,207 A | 7/1996 | Wong et al. |
| 5,552,997 A | 9/1996 | Massart |
| 5,559,504 A | 9/1996 | Itsumi et al. |
| 5,568,251 A | 10/1996 | Davies et al. |
| 5,596,992 A | 1/1997 | Haaland et al. |
| 5,606,164 A | 2/1997 | Price et al. |
| 5,613,014 A | 3/1997 | Eshera et al. |
| 5,630,413 A | 5/1997 | Thomas et al. |
| 5,636,633 A | 6/1997 | Messerschmidt et al. |
| 5,655,530 A | 8/1997 | Messerschmidt |
| 5,672,864 A | 9/1997 | Kaplan |
| 5,672,875 A | 9/1997 | Block et al. |
| 5,677,762 A | 10/1997 | Ortyn et al. |
| 5,681,273 A | 10/1997 | Brown |
| 5,708,593 A | 1/1998 | Saby et al. |
| 5,719,399 A | 2/1998 | Alfano et al. |
| 5,719,950 A | 2/1998 | Osten et al. |
| 5,724,268 A | 3/1998 | Sodickson et al. |
| 5,729,619 A | 3/1998 | Puma |
| 5,737,439 A | 4/1998 | Lapsley et al. |
| 5,743,262 A | 4/1998 | Lepper, Jr. et al. |
| 5,747,806 A | 5/1998 | Khalil |
| 5,750,994 A | 5/1998 | Schlager |
| 5,751,835 A | 5/1998 | Topping et al. |
| 5,751,836 A | 5/1998 | Wildes et al. |
| 5,761,330 A | 6/1998 | Stoianov et al. |
| 5,782,755 A | 7/1998 | Chance et al. |
| 5,792,050 A | 8/1998 | Alam et al. |
| 5,792,053 A | 8/1998 | Skladnev et al. |
| 5,793,881 A | 8/1998 | Stiver et al. |
| 5,796,858 A | 8/1998 | Zhou et al. |
| 5,808,739 A | 9/1998 | Turner et al. |
| 5,818,048 A | 10/1998 | Sodickson et al. |
| 5,823,951 A | 10/1998 | Messerschmidt et al. |
| 5,828,066 A | 10/1998 | Messerschmidt |
| 5,830,132 A | 11/1998 | Robinson |
| 5,830,133 A | 11/1998 | Osten et al. |
| 5,850,623 A | 12/1998 | Carman, Jr. et al. |
| 5,853,370 A | 12/1998 | Chance et al. |
| 5,857,462 A | 1/1999 | Thomas et al. |
| 5,859,420 A | 1/1999 | Borza |
| 5,860,421 A | 1/1999 | Eppstein et al. |
| 5,867,265 A | 2/1999 | Thomas |
| 5,886,347 A | 3/1999 | Inoue et al. |
| 5,902,033 A | 5/1999 | Levis et al. |
| 5,914,780 A | 6/1999 | Turner et al. |
| 5,929,443 A | 7/1999 | Alfano et al. |
| 5,933,792 A | 8/1999 | Anderson et al. |
| 5,935,062 A | 8/1999 | Messerschmidt et al. |
| 5,945,676 A | 8/1999 | Khalil |
| 5,949,543 A | 9/1999 | Bleier et al. |
| 5,957,841 A | 9/1999 | Maruo et al. |
| 5,961,449 A | 10/1999 | Toida et al. |
| 5,963,319 A | 10/1999 | Jarvis et al. |
| 5,978,495 A | 11/1999 | Thomopoulos et al. |
| 5,987,346 A | 11/1999 | Benaron et al. |
| 5,999,637 A | 12/1999 | Toyoda et al. |
| 6,005,722 A | 12/1999 | Butterworth et al. |
| 6,016,435 A | 1/2000 | Maruo et al. |
| 6,025,597 A | 2/2000 | Sterling et al. |
| 6,026,314 A | 2/2000 | Amerov et al. |
| 6,028,773 A | 2/2000 | Hundt |
| 6,031,609 A | 2/2000 | Funk et al. |
| 6,034,370 A | 3/2000 | Messerschmidt |
| 6,040,578 A | 3/2000 | Malin et al. |
| 6,041,247 A | 3/2000 | Weckstrom et al. |
| 6,041,410 A * | 3/2000 | Hsu et al. ..................... 713/186 |
| 6,043,492 A | 3/2000 | Lee et al. |
| 6,044,285 A | 3/2000 | Chaiken et al. |
| 6,045,502 A | 4/2000 | Eppstein et al. |
| 6,046,808 A | 4/2000 | Fateley |
| 6,049,727 A | 4/2000 | Crothall |
| 6,056,738 A | 5/2000 | Marchitto et al. |
| 6,057,925 A | 5/2000 | Anthon |
| 6,061,581 A | 5/2000 | Alam et al. |

| | | | |
|---|---|---|---|
| 6,061,582 A | 5/2000 | Small et al. |
| 6,066,847 A | 5/2000 | Rosenthal |
| 6,069,689 A | 5/2000 | Zeng et al. |
| 6,070,093 A | 5/2000 | Oosta et al. |
| 6,073,037 A | 6/2000 | Alam et al. |
| 6,081,612 A | 6/2000 | Gutkowicz-Krusin et al. |
| 6,088,605 A | 7/2000 | Griffith et al. |
| 6,088,607 A | 7/2000 | Diab et al. |
| 6,097,035 A | 8/2000 | Belongie et al. |
| 6,100,811 A | 8/2000 | Hsu et al. |
| 6,115,484 A | 9/2000 | Bowker et al. |
| 6,115,673 A | 9/2000 | Malin et al. |
| 6,122,042 A | 9/2000 | Wunderman et al. |
| 6,122,394 A | 9/2000 | Neukermans et al. |
| 6,122,737 A | 9/2000 | Bjorn et al. |
| 6,125,192 A | 9/2000 | Bjorn et al. |
| 6,141,101 A | 10/2000 | Bleier et al. |
| 6,147,749 A | 11/2000 | Kubo et al. |
| 6,148,094 A | 11/2000 | Kinsella |
| 6,152,876 A | 11/2000 | Robinson et al. |
| 6,154,658 A | 11/2000 | Caci |
| 6,157,041 A | 12/2000 | Thomas et al. |
| 6,159,147 A | 12/2000 | Lichter et al. |
| 6,172,743 B1 | 1/2001 | Kley et al. |
| 6,175,407 B1* | 1/2001 | Sartor ............................ 356/71 |
| 6,181,414 B1 | 1/2001 | Raz et al. |
| 6,181,958 B1 | 1/2001 | Steuer et al. |
| 6,188,781 B1 | 2/2001 | Brownlee |
| 6,193,153 B1 | 2/2001 | Lambert |
| 6,208,749 B1 | 3/2001 | Gutkowicz-Krusin |
| 6,212,424 B1 | 4/2001 | Robinson |
| 6,226,541 B1 | 5/2001 | Eppstein et al. |
| 6,229,908 B1 | 5/2001 | Edmonds et al. |
| 6,230,034 B1 | 5/2001 | Messerschmidt et al. |
| 6,236,047 B1 | 5/2001 | Malin et al. |
| 6,240,306 B1 | 5/2001 | Rohrscheib et al. |
| 6,240,309 B1 | 5/2001 | Yamashita et al. |
| 6,241,663 B1 | 6/2001 | Wu et al. |
| 6,256,523 B1 | 7/2001 | Diab et al. |
| 6,272,367 B1 | 8/2001 | Chance |
| 6,280,381 B1 | 8/2001 | Malin et al. |
| 6,282,303 B1 | 8/2001 | Brownlee |
| 6,285,895 B1 | 9/2001 | Ristolainen et al. |
| 6,292,576 B1 | 9/2001 | Brownlee |
| 6,301,375 B1 | 10/2001 | Choi |
| 6,301,815 B1 | 10/2001 | Sliwa |
| 6,304,767 B1 | 10/2001 | Soller et al. |
| 6,307,633 B1 | 10/2001 | Mandella et al. |
| 6,309,884 B1 | 10/2001 | Cooper et al. |
| 6,317,507 B1 | 11/2001 | Dolfing et al. |
| 6,324,310 B1 | 11/2001 | Brownlee |
| 6,330,346 B1 | 12/2001 | Peterson et al. |
| 6,404,904 B1 | 6/2002 | Einighammer et al. |
| 6,419,361 B2 | 7/2002 | Cabib et al. |
| 6,483,929 B1 | 11/2002 | Murakami et al. |
| 6,504,614 B1 | 1/2003 | Messerschmidt et al. |
| 6,537,225 B1 | 3/2003 | Mills |
| 6,560,352 B2 | 5/2003 | Rowe et al. |
| 6,574,490 B2 | 6/2003 | Abbink et al. |
| 6,597,945 B2 | 7/2003 | Marksteiner |
| 6,606,509 B2 | 8/2003 | Schmitt |
| 6,628,809 B1 | 9/2003 | Rowe et al. |
| 6,631,199 B1 | 10/2003 | Topping et al. |
| 6,741,729 B2 | 5/2004 | Bjorn et al. |
| 6,749,115 B2 | 6/2004 | Gressel et al. |
| 6,799,275 B1 | 9/2004 | Bjorn |
| 6,799,726 B2 | 10/2004 | Stockhammer |
| 6,816,605 B2 | 11/2004 | Rowe et al. |
| 6,825,930 B2 | 11/2004 | Cronin et al. |
| 6,853,444 B2 | 2/2005 | Haddad |
| 6,898,299 B1 | 5/2005 | Brooks |
| 6,928,181 B2 | 8/2005 | Brooks |
| 6,937,885 B1 | 8/2005 | Lewis et al. |
| 6,958,194 B1 | 10/2005 | Hopper et al. |
| 6,995,384 B2 | 2/2006 | Lee et al. |
| 7,047,419 B2 | 5/2006 | Black |
| 7,084,415 B2 | 8/2006 | Iwai |
| 7,147,153 B2 | 12/2006 | Rowe et al. |
| 7,254,255 B2 | 8/2007 | Dennis |
| 7,263,213 B2 | 8/2007 | Rowe |
| 7,287,013 B2 | 10/2007 | Schneider et al. |
| 7,347,365 B2 | 3/2008 | Rowe |
| 7,366,331 B2 | 4/2008 | Higuchi |
| 7,386,152 B2 | 6/2008 | Rowe et al. |
| 7,394,919 B2 | 7/2008 | Rowe et al. |
| 7,397,943 B2 | 7/2008 | Merbach et al. |
| 7,440,597 B2 | 10/2008 | Rowe |
| 7,460,696 B2 | 12/2008 | Rowe |
| 7,508,965 B2 | 3/2009 | Rowe et al. |
| 7,515,252 B2 | 4/2009 | Hernandez |
| 7,539,330 B2 | 5/2009 | Rowe |
| 7,545,963 B2* | 6/2009 | Rowe ........................... 382/124 |
| 7,627,151 B2 | 12/2009 | Rowe |
| 7,668,350 B2 | 2/2010 | Rowe |
| 7,735,729 B2 | 6/2010 | Rowe |
| 7,751,594 B2 | 7/2010 | Rowe et al. |
| 7,801,338 B2 | 9/2010 | Rowe |
| 7,801,339 B2 | 9/2010 | Sidlauskas et al. |
| 7,804,984 B2 | 9/2010 | Sidlauskas et al. |
| 7,819,311 B2 | 10/2010 | Rowe et al. |
| 7,831,072 B2 | 11/2010 | Rowe |
| 7,835,554 B2* | 11/2010 | Rowe ........................... 382/124 |
| 7,899,217 B2 | 3/2011 | Uludag et al. |
| 7,995,808 B2 | 8/2011 | Rowe et al. |
| 2002/0009213 A1 | 1/2002 | Rowe et al. |
| 2002/0065468 A1 | 5/2002 | Utzinger et al. |
| 2002/0101566 A1 | 8/2002 | Elsner et al. |
| 2002/0111546 A1 | 8/2002 | Cook et al. |
| 2002/0138768 A1 | 9/2002 | Murakami et al. |
| 2002/0171834 A1 | 11/2002 | Rowe et al. |
| 2002/0183624 A1 | 12/2002 | Rowe et al. |
| 2003/0025897 A1 | 2/2003 | Iwai |
| 2003/0044051 A1* | 3/2003 | Fujieda ........................ 382/124 |
| 2003/0078504 A1 | 4/2003 | Rowe |
| 2003/0095525 A1 | 5/2003 | Lavin et al. |
| 2003/0128867 A1 | 7/2003 | Bennett |
| 2003/0163710 A1* | 8/2003 | Ortiz et al. .................... 713/186 |
| 2003/0223621 A1 | 12/2003 | Rowe et al. |
| 2004/0003295 A1 | 1/2004 | Elderfield et al. |
| 2004/0008875 A1 | 1/2004 | Linares |
| 2004/0022421 A1 | 2/2004 | Endoh et al. |
| 2004/0042642 A1 | 3/2004 | Bolle et al. |
| 2004/0047493 A1 | 3/2004 | Rowe et al. |
| 2004/0068394 A1 | 4/2004 | Maekawa et al. |
| 2004/0114783 A1 | 6/2004 | Spycher et al. |
| 2004/0120553 A1 | 6/2004 | Stobbe |
| 2004/0125994 A1 | 7/2004 | Engels et al. |
| 2004/0179722 A1 | 9/2004 | Moritoki et al. |
| 2004/0240712 A1 | 12/2004 | Rowe et al. |
| 2004/0240713 A1 | 12/2004 | Hata |
| 2004/0264742 A1 | 12/2004 | Zhang et al. |
| 2005/0007582 A1 | 1/2005 | Villers et al. |
| 2005/0125339 A1 | 6/2005 | Tidwell et al. |
| 2005/0169504 A1 | 8/2005 | Black |
| 2005/0180620 A1 | 8/2005 | Takiguchi |
| 2005/0185847 A1 | 8/2005 | Rowe |
| 2005/0205667 A1 | 9/2005 | Rowe |
| 2005/0265585 A1 | 12/2005 | Rowe |
| 2005/0265586 A1 | 12/2005 | Rowe et al. |
| 2005/0265607 A1 | 12/2005 | Chang |
| 2005/0271258 A1 | 12/2005 | Rowe |
| 2006/0002597 A1 | 1/2006 | Rowe |
| 2006/0002598 A1 | 1/2006 | Rowe et al. |
| 2006/0045330 A1 | 3/2006 | Marion |
| 2006/0062438 A1 | 3/2006 | Rowe |
| 2006/0110015 A1 | 5/2006 | Rowe |
| 2006/0115128 A1 | 6/2006 | Mainguet |
| 2006/0171571 A1 | 8/2006 | Chan et al. |
| 2006/0173256 A1* | 8/2006 | Ridder et al. ................ 600/316 |
| 2006/0202028 A1 | 9/2006 | Rowe |
| 2006/0210120 A1 | 9/2006 | Rowe |
| 2006/0244947 A1 | 11/2006 | Rowe |
| 2006/0274921 A1* | 12/2006 | Rowe ........................... 382/124 |
| 2007/0014437 A1 | 1/2007 | Sato |
| 2007/0030475 A1 | 2/2007 | Rowe et al. |
| 2007/0052827 A1 | 3/2007 | Hiltunen |
| 2007/0116331 A1 | 5/2007 | Rowe et al. |
| 2007/0153258 A1 | 7/2007 | Hernandez |

| | | | |
|---|---|---|---|
| 2007/0165903 A1 | 7/2007 | Munro et al. | |
| 2008/0008359 A1 | 1/2008 | Beenau et al. | |
| 2008/0013806 A1 | 1/2008 | Hamid | |
| 2008/0025579 A1* | 1/2008 | Sidlauskas et al. | 382/124 |
| 2008/0025580 A1* | 1/2008 | Sidlauskas et al. | 382/124 |
| 2008/0192988 A1 | 8/2008 | Uludag et al. | |
| 2008/0260211 A1 | 10/2008 | Bennett et al. | |
| 2008/0298649 A1 | 12/2008 | Ennis et al. | |
| 2009/0046903 A1 | 2/2009 | Corcoran et al. | |
| 2009/0080709 A1 | 3/2009 | Rowe et al. | |
| 2009/0092290 A1 | 4/2009 | Rowe | |
| 2009/0148005 A1 | 6/2009 | Rowe | |
| 2009/0245591 A1* | 10/2009 | Rowe et al. | 382/115 |
| 2010/0067748 A1 | 3/2010 | Rowe | |
| 2010/0246902 A1 | 9/2010 | Rowe et al. | |
| 2011/0085708 A1 | 4/2011 | Martin et al. | |
| 2011/0211055 A1 | 9/2011 | Martin et al. | |
| 2011/0235872 A1 | 9/2011 | Rowe et al. | |

FOREIGN PATENT DOCUMENTS

| | | |
|---|---|---|
| CN | 1402183 A | 3/2003 |
| CN | 1509454 A | 6/2004 |
| DE | 10153808 | 5/2003 |
| EP | 0 280 418 A1 | 8/1988 |
| EP | 0 372 748 | 6/1990 |
| EP | 0 426 358 B1 | 5/1991 |
| EP | 0 449 335 A2 | 10/1991 |
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 757 243 A1 | 2/1997 |
| EP | 0 788 000 A2 | 8/1997 |
| EP | 0 801 297 A1 | 10/1997 |
| EP | 0 836 083 A1 | 4/1998 |
| EP | 0 843 986 A2 | 5/1998 |
| EP | 0 869 348 A2 | 10/1998 |
| EP | 0 897 164 A2 | 2/1999 |
| EP | 0 897 691 A2 | 2/1999 |
| EP | 0 317 121 B1 | 5/1999 |
| EP | 0 924 656 A2 | 6/1999 |
| EP | 0 982 583 A1 | 3/2000 |
| EP | 0 990 945 A1 | 4/2000 |
| EP | 1 353 292 | 10/2003 |
| EP | 1 434 162 A2 | 6/2004 |
| FR | 2761180 A1 | 9/1998 |
| JP | 61182174 A | 8/1986 |
| JP | 3016160 | 1/1991 |
| JP | 7075629 A | 3/1995 |
| JP | 10-127585 | 5/1998 |
| JP | 2001033381 A | 2/2001 |
| JP | 2001-112742 | 4/2001 |
| JP | 2001-184490 A | 7/2001 |
| JP | 2002-133402 A | 5/2002 |
| JP | 2002-517835 A | 6/2002 |
| JP | 2003050993 A | 2/2003 |
| JP | 2003-511101 A | 3/2003 |
| JP | 2003-308520 A | 10/2003 |
| WO | WO 92/00513 A1 | 1/1992 |
| WO | WO 92/17765 A1 | 10/1992 |
| WO | WO 93/00855 A1 | 1/1993 |
| WO | WO 93/07801 A1 | 4/1993 |
| WO | WO 99/27848 A1 | 6/1999 |
| WO | WO 00/30530 | 6/2000 |
| WO | WO 00/46739 A1 | 8/2000 |
| WO | WO 01/15596 A1 | 3/2001 |
| WO | WO 01/18332 A1 | 3/2001 |
| WO | WO 01/20538 | 3/2001 |
| WO | WO 01/27882 A2 | 4/2001 |
| WO | WO 01/52180 A1 | 7/2001 |
| WO | WO 01/52726 A1 | 7/2001 |
| WO | WO 01/53805 A1 | 7/2001 |
| WO | WO 01/65471 A | 9/2001 |
| WO | WO 01/69520 A2 | 9/2001 |
| WO | WO 02/054337 A1 | 7/2002 |
| WO | WO 02/084605 A2 | 10/2002 |
| WO | WO 02/099393 A2 | 12/2002 |
| WO | WO 03/010510 A2 | 2/2003 |
| WO | WO 03/096272 A1 | 11/2003 |
| WO | WO 2004/068388 A2 | 8/2004 |
| WO | WO 2004/068394 A1 | 8/2004 |
| WO | WO 2004/090786 | 10/2004 |
| WO | WO 2006/049394 A | 5/2006 |
| WO | WO 2006/077446 A2 | 7/2006 |
| WO | WO 2006/093508 A2 | 9/2006 |

OTHER PUBLICATIONS

Rowe, "LumiGuard: A Novel Spectroscopic Sensor for Biometric Security Applications", American Chemical Society 225th National Meeting, Mar. 25, 2003, 20 pages.

International Search Report and Written Opinion of PCT/US2008/066585 mailed Oct. 30, 2008, 10 pages.

International Search Report of PCT/US2010/046852 mailed Dec. 29, 2010, 5 pages.

Anderson, C. E. et al., "Fundamentals of Calibration Transfer Through Procrustes Analysis," Appln. Spectors., vol. 53, No. 10 (1999) p. 1268-1276.

Ashboum, Julian, Biometrics; Advanced Identity Verification, Springer, 2000, pp. 63-64).

Bantle, John P. et al., "Glucose Measurement in Patients With Diabetes Mellitus With Dermal Interstitial Fluid," Mosby-Year Book, Inc., 9 pages, 1997.

Berkoben, Michael S. et al., "Vascular Access for Hemodialysis," Clinical Dialysis, Third Edition, pp. 2 cover pages and 26-45, 1995.

Blank, T.B. et al., "Transfer of Near-Infrared Multivariate Calibrations Without Standards," Anal. Chem., vol. 68 (1996) p. 2987.

Bleyer, Anthony J. et al., "The Costs of Hospitalizations Due To Hemodialysis Access Management," Nephrology News & Issues, pp. 19, 20 and 22, Jan. 1995.

Brasunas John C. et al., "Uniform Time-Sampling Fourier Transform Spectroscopy," Applied Optics, vol. 36, No. 10, Apr. 1, 1997, pp. 2206-2210.

Brault, James W., "New Approach to High-Precision Fourier Transform Spectrometer Design," Applied Optics, Vo. 35, No. 16, Jun. 1, 1996, pp. 2891-2896.

Brochure entitled "Improve the Clinical Outcome of Every Patient", In Line Diagnostics, published on or before Oct. 30, 1997, 2 pages.

Cassarly, W.J. et al., "Distributed Lighting Systems: Uniform Light Delivery," Source Unknown, pp. 1698-1702.

Chang, Chong-Min et al., "An Uniform Rectangular Immuminating Optical System for Liquid Crystal Light Valve Projectors," Euro Display '96 (1996) pp. 257-260.

Coyne, Lawrence J. et al., "Distributive Fiber Optic couplers Using Rectangular Lightguides as Mixing Elements," (Information Gatekeepers, Inc. Brookline, MA, 1979) pp. 160-164.

Daugirdas, JT et al., "Comparison of Methods To Predict the Equilibrated Kt/V (eKt/V) in the Hemo Study," National Institutes of Health, pp. 1-28, Aug. 20, 1996.

de Noord, Onno E., "Multivariate Calibration Standardization," Chemometrics and intelligent Laboratory Systems 25, (1994) pp. 85-97.

Demos, S. G. et al., "Optical Fingerprinting Using Polarisation Contrast Improvement," Electronics Letters, vol. 33, No. 7, pp. 582-584, Mar. 27, 1997.

Depner, Thomas A. et al., "Clinical Measurement of Blood Flow in Hemodialysis Access Fistulae and Grafts by Ultrasound Dilution," Division of Nephrology, University of California, pp. M745-M748, published on of before Oct. 30, 1997.

Despain, Alvin M. et al., "A Large-Aperture Field-Widened Interferometer-Spectrometer for Airglow Studies," Aspen International Conference on Fourier Spectroscopy, 1970, pp. 293-300.

Faber, Nicolaas, "Multivariate Sensitivity for the Interpretation of the Effect of Spectral Pretreatment Methods on Near-Infrared Calibration Model Predictions," Analytical Chemistry, vol. 71, No. 3, Feb. 1, 1999, pp. 557-565.

Fresenius USA, "Determination of Delivered Therapy Through Measurement of Effective Clearance," 2 pages, Dec. 1994.

Geladi, Paul et al., A Multivariate NIR Study of Skin Alterations in Diabetic Patients as Compared to Control Subjects, J. Near Infrared Spectrosc., vol. 8 (2000) pp. 217-227.

Hakim, Raymond M. et al., "Effects of Dose of Dialysis on Morbidity and Mortality," American Journal of Kidney Diseases, vol. 23, No. 5, pp. 661-669, May 1994.

Jacobs, Paul et al., "A Disposable Urea Sensor for Continuous Monitoring of Hemodialysis Efficiency," ASAIO Journal, pp. M353-M358, 1993.

Keshaviah, Prakash R. et al., "On-Line Monitoring of the Delivery of the Hemodialysis Prescription," Pediatric Nephrology, vol. 9, pp. S2-S8, 1995.

Krivitski, Nikolai M., "Theory and Validation of Access Flow Measurement by Dilution Technique During Hemodialysis," Kidney International, vol. 48, pp. 244-250, 1995.

Lee et al., "Fingerprint Recognition Using Principal Gabor Basis Function", Proceedings of 2001 International Symposium on Intelligent Multimedia, Video and Speech Processing, May 2-4, 2001, Sections 2-3.

Marbach, Ralf, "Measurement Techniques for IR Spectroscopic Blood Glucose Determination," Fortschritt Bericht, Series 8: Measurement and Control Technology, No. 346, pp. cover and 1-158, Mar. 28, 1994.

Mardia, K.V. et al., "Chapter 11—Discriminant Analysis," Multivariate Analysis, pp. 2 cover pages and 300-325, 1979.

Nichols, Michael G. et al., "Design and Testing of a White-Light, Steady-State Diffuse Reflectance Spectrometer for Determination of Optical Properties of Highly Scattering Systems," Applied Optics, vol. 36, No. 1, pp. 93-104, Jan. 1, 1997.

Nixon, Kristin A. et al., "Novel Spectroscopy-Based Technology for Biometric and Liveness Verification", Technology for Human Identification. Proceedings od SPIE, vol. 5404, No. 1, XP-002458441, Apr. 12-13, 2004, pp. 287-295 (ISSN: 0277-786x).

Pan et al., "Face Recognition in Hyperspectral Images", IEEE Transactions on Pattern Analysis and Machine Intelligence vol. 25, No. 12, Dec. 2003.

Ripley, B. D., "Chapter 3—Linear Discriminant Analysis," Pattern Recognition and Neural Networks, pp. 3 cover pages and 91-120, 1996.

Ronco, C. et al., "On-Line Urea Monitoring : A Further Step Towards Adequate Dialysis Prescription and Delivery," The International Journal of Artificial Organs, vol. 18, No. 9, pp. 534-543, 1995.

Ross et al., "A Hybrid Fingerprint Matcher," Pattern Recognition 36, The Journal of the Pattern Recognition Society, 2003 Elsevier Science Ltd., pp. 1661-1673.

Selvaraj et al., Fingerprint Verification Using Wavelet Transform, Proceedings of the Fifth International Conference on Computational Intelligence and Multimedia Applications, IEEE, 2003.

Service, F. John et al., "Dermal Interstitial Glucose as an Indicator of Ambient Glycemia," Diabetes Care, vol. 20, No. 9, 8 pages, Aug. 1997.

Sherman, Richard A., "Chapter 4—Recirculation in the Hemodialysis Access," Principles and Practice of Dialysis, pp. 2 cover pages and 38-46, 1994.

Sherman, Richard A., "The Measurement of Dialysis Access Recirculation," American Journal of Kidney Diseases, vol. 22, No. 4, pp. 616-621, Oct. 1993.

Steuer, Robert R. et al., "A New Optical Technique for Monitoring Hematocrit and Circulating Blood Volume: Its Application in Renal Dialysis," Dialysis & Transplantation, vol. 22, No. 5, pp. 260-265, May 1993.

Webb, Paul, "Temperature of Skin, Subcutaneous Tissue, Muscle and Core in Resting Men in Cold, Comfortable and Hot Conditions," European Journal of Applied Physiology, vol. 64, pp. 471-476, 1992.

Zavala, Albert et al., "Using Fingerprint Measures to Predict Other Anthropometric Variables," Human Factors, vol. 17, No. 6, pp. 591-602, 1975.

Chinese Patent Application No. 2006/80038597.4, First Office Action mailed on Mar. 23, 2011, 7 pages.

European Patent Application No. 10166537.0, Extended European Search Report mailed on Jun. 1, 2011, 7 pages.

International Search Report and Written Opinion of PCT/US2010/025463 mailed on Jun. 30, 2010, 12 pages.

Rowe, et al. "Multispectral Fingerprint Image Acquisition," Advance in Biometrics, 2008, 22 pages.

Meltoni et al., "Handbook of Fingerprint Recognition," 2005, pp. 58-61.

* cited by examiner

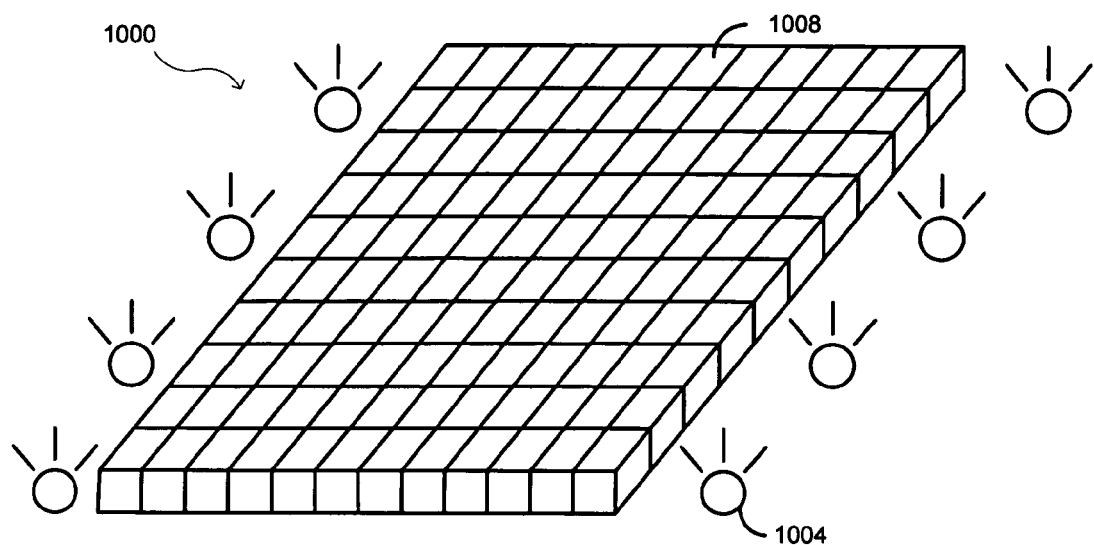
Fig. 10A
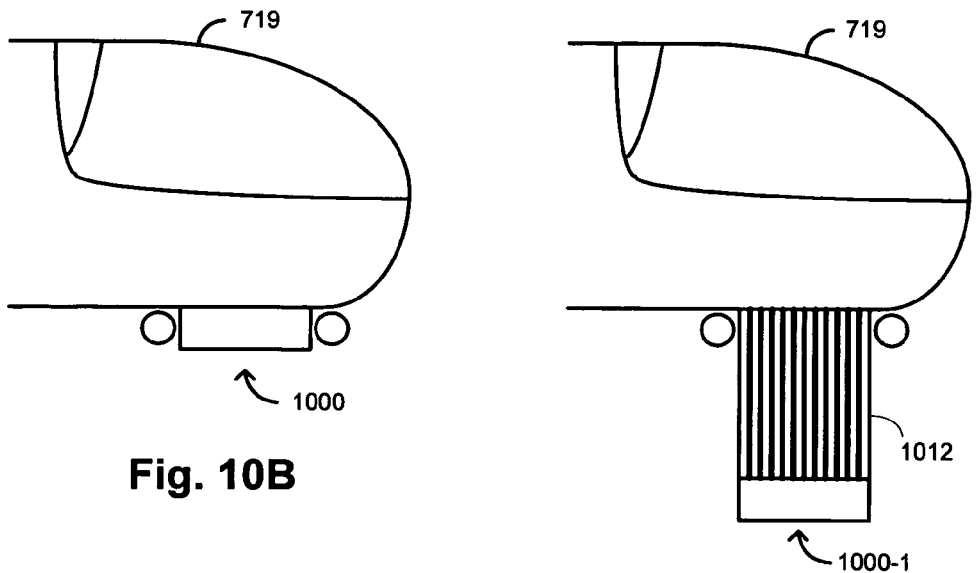
Fig. 10B
Fig. 10C

BIOMETRICS BASED ON LOCALLY CONSISTENT FEATURES

CROSS REFERENCES

This application claims priority from U.S. Provisional Patent Application No. 60/896,063, filed Mar. 21, 2007, entitled "BIOMETRICS BASED ON MULTISPECTRAL SKIN TEXTURE", which is hereby incorporated by reference, as if set forth in full in this document, for all purposes. This application is related to each of the following co-pending, commonly assigned applications, the entire disclosure of each of which is incorporated herein by reference for all purposes: U.S. patent application Ser. No. 11/219,006, entitled "COMPARATIVE TEXTURE ANALYSIS OF TISSUE FOR BIOMETRIC SPOOF DETECTION," filed Sep. 1, 2005 by Robert K. Rowe; and U.S. patent application Ser. No. 11/458,619, entitled "TEXTURE-BIOMETRICS SENSOR," filed Jul. 19, 2006 by Robert K. Rowe.

BACKGROUND

The present invention relates to biometrics in general and, in particular, to biometrics based on multispectral skin texture.

Fingerprint-based biometric sensors are used across a broad range of applications, from law enforcement and civil identification to commercial access control. They are even used in some consumer devices such as laptops and cellular telephones. In at least some of these applications, there is a general need in the art to reduce the overall size of the sensor in order to reduce the area of the device that the sensor occupies, as well as to reduce the overall cost of the sensor.

Most fingerprint sensors work by imaging a fingerprint and comparing the image to one or more stored images in a database. As such, when a large area of the fingerprint is imaged, more data may be compared and more discriminating results may be obtained. Conversely, the performance of these types of fingerprint sensors may degrade as their sizes decrease.

One way to accommodate this concern may be to produce long, narrow fingerprint sensors that simulate a larger-area sensor by combining a series of narrow images collected while the user swipes a finger across the sensor surface. Another, similar way to accommodate this concern may be to piece together a set of smaller images of a fingerprint to collectively form a larger fingerprint image (called "mosaiking"). Such configurations may reduce the sensor size, but they may also place additional burdens on the user (e.g., requiring the user to learn how to swipe a fingerprint or requiring precise locating of the finger on the sensor) and may limit the applications in which such a sensor may be employed.

It may be desirable, therefore, to provide a reduced-size biometric sensor that may be highly usable and employed in a wide variety of applications without a significant degradation in functionality or usability.

SUMMARY

Among other things, methods, systems, and devices are described for biometric sensors that permit a reduction in the size of the sensing area without significant reduction in biometric functionality of the sensor.

Embodiments of the invention achieve a reduction in sensing area of a biometric sensor by measuring a property of the skin that is locally consistent while still being distinct between different people. Because the property is locally consistent, measurements at an enrollment skin location and at a measurement site may be meaningfully compared even if the enrollment and measurement sites are different. In some embodiments, the property comprises an optical property of the skin. In particular, certain embodiments use a range of spatiospectral imaging techniques with small-area sensors. Matching may be done using spatial, spectral, and/or textural descriptors of the imaging data combined with a classification methodology that applies characteristics of the data that are locally consistent.

In some embodiments, spatial information is detected. For example, different spacings may be provided between light sources and imagers to look for spatial illumination signatures (e.g., "roll-off"). In other embodiments, spectral information is detected. For example, at a fixed spacing between the light source and the imager, different frequency compositions may be obtained by using various illumination wavelengths, polarizations, filters, and other characteristics of illumination. Further, the spectral information may be detected and/or used in many different ways, including pixel-by-pixel, on average over a certain window of pixels, as summarized by various frequency decomposition methods, etc. In still other embodiments, textural information is detected. In some configurations, the textural information may indicate optical features (e.g., lumpiness, ridge spacing, etc.); while in other configurations, the textural information may indicate features of the spatial and/or spectral data (e.g., the distribution of coefficents derived from a Fourier decomposition of one or more multispectral image regions). In yet other embodiments, multiple types of information are detected simultaneously or in series, and are used in conjunction for a variety of situations. In even other embodiments, the sensor or other components may be operable to "learn" over time. For example, each time a user is identified, the biometric information may be processed, along with some or all of the previous biometric information gathered from that user. The combined information may be used to generate a more discriminatory biometric profile for that user.

One set of embodiments provides a method of performing a biometric function. The method includes illuminating a small-area purported skin site of an individual with illumination light, wherein the small-area purported skin site is in contact with a surface; receiving light scattered from the small-area purported skin site, wherein the light is received substantially in a region that includes the surface; generating a local feature profile from the received light, wherein the local feature profile identifies a feature of the small-area purported skin site, the feature of the small-area purported skin site being of a type predetermined to exhibit substantial local consistency; and analyzing the generated local feature profile to perform the biometric function. Analyzing the generated local feature profile includes comparing the generated local feature profile with a reference local feature profile, wherein the reference local feature profile was generated from light scattered from a small-area reference skin site, and the small-area purported skin site is substantially different from the reference small-area skin site.

Another set of embodiments provides a biometric sensor. The biometric sensor includes a surface adapted for contact with a purported skin site of an individual; an illumination subsystem disposed to illuminate the purported skin site; a detection subsystem disposed to receive light scattered from the purported skin site, wherein the light is received substantially in a region that includes the surface; and a computational unit interfaced with the detection subsystem. The computational unit has instructions for forming an image from the received light; instructions for generating an image-texture measure from the image; and instructions for analyzing the generated image-texture measure to perform the biometric function.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 10A shows a simplified perspective view of an MSI sensor having a number of light sources arranged around a detector array, according to various embodiments of the invention.

FIG. 10B shows a simplified side view of an embodiment of an MSI sensor, like the one in FIG. 10A, where the imager is substantially in contact with the skin site, according to various embodiments of the invention.

FIG. 10C shows a simplified side view of an embodiment of an MSI sensor, like the one in FIG. 10A, where the imager is displaced from the skin site, according to various embodiments of the invention.

DETAILED DESCRIPTION OF THE INVENTION

Figure 1:
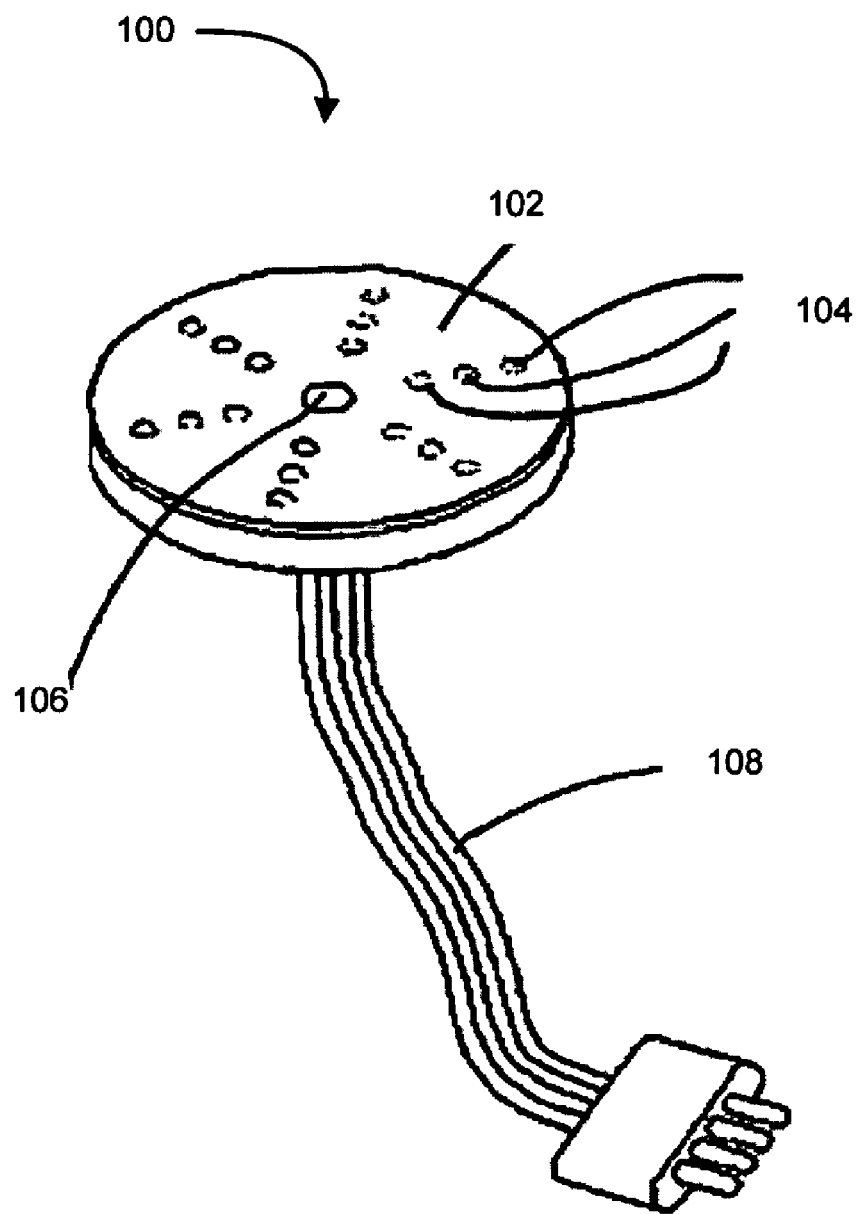
FIG. 1 shows a simplified perspective view of an embodiment of an exemplary small-area sensor, according to various embodiments of the present invention.

Systems, devices, methods, and software are described for biometric sensors that permit a reduction in the size of the sensing area without significant reduction in biometric functionality of the sensor. It may be desirable to provide a small-area sensor for a number of reasons. For example, many applications may be limited by size (e.g., by form factor), by power consumption (e.g., by battery life), by cost, or by some other limitation. It will further be appreciated that providing a small, but reliable, sensor may allow the sensor to be used in many applications, including laptops, cell phones, car keys, garage door openers, locks, industrial machine switches, or any other application where it may be desirable to obtain biometric information or to restrict access.

One way to reduce the sensing area while maintaining a simple, single-touch user interface may be to measure a property of the skin that is locally consistent while still being distinct from person to person. In this way, a small-area sensor may be able to perform a biometric match using a skin location never previously enrolled as long as the optical properties of the enrolled and tested skin sites were "similar enough."

Embodiments of the invention provide methods and systems that allow for the collection and processing of a variety of different types of biometric measurements, including integrated, multifactor biometric measurements in some embodiments. These measurements may provide strong assurance of a person's identity, as well as of the authenticity of the biometric sample being taken.

Skin composition and structure is very distinct, very complex, and varies from person to person. By performing optical measurements of spatio-spectral properties of skin and underlying tissue, a number of assessments may be made. For example, a biometric-identification function may be performed to identify or verify whose skin is being measured, a liveness function may be performed to assure that the sample being measured is live and viable skin and not another type of material, estimates may be made of a variety of physiological parameters such as age, gender, ethnicity, and other demographic and anthropometric characteristics, and/or measurements may be made of the concentrations of various analytes and parameters including alcohol, glucose, degrees of blood perfusion and oxygenation, bilirubin, cholesterol, urea, and the like.

The complex structure of skin may be used in different embodiments to tailor aspects of the methods and systems for particular functions. The outermost layer of skin, the epidermis, is supported by the underlying dermis and hypodermis. The epidermis itself may have identified sub-layers that include the stratum corneum, the stratum lucidum, the stratum granulosum, the stratum spinosum, and the stratum germinativum. Thus, for example, the skin below the top-most stratum corneum has some characteristics that relate to the surface topography, as well as some characteristics that change with depth into the skin. While the blood supply to skin exists in the dermal layer, the dermis has protrusions into the epidermis known as "dermal papillae," which bring the blood supply close to the surface via capillaries. In the volar surfaces of the fingers, this capillary structure follows the pattern of the friction ridges and valleys on the surface. In some other locations on the body, the structure of the capillary bed may be less ordered, but is still characteristic of the particular location and person.

As well, the topography of the interface between the different layers of skin is complex and characteristic of the skin location and the person. While these sources of subsurface structure of skin and underlying tissue may represent a significant noise source for non-imaging optical measurements of skin for biometric determinations or analyte measurements, the structural differences may be manifested by spatiospectral features that can be compared through embodiments of the invention.

In some instances, inks, dyes, and/or other pigmentation may be present in portions of the skin as topical coating or subsurface tattoos. These forms of artificial pigmentation may or may not be visible to the naked human eye. However, if one or more wavelengths used by the apparatus of the present invention is sensitive to the pigment, the sensor can be used in some embodiments to verify the presence, quantity, and/or shape of the pigment in addition to other desired measurement tasks.

In general, embodiments of the present invention provide methods and systems that collect spatio-spectral information that may be represented in a multidimensional data structure that has independent spatial and spectral dimensions. In certain instances, the desired information is contained in just a portion of the entire multidimensional data structure. For example, estimation of a uniformly distributed, spectrally active compound may require just the measured spectral characteristics, which may be extracted from the overall multidimensional data structure. In such cases, the overall system design may be simplified to reduce or eliminate the spatial component of the collected data by reducing the number of image pixels, even to a limit of a single pixel. Thus, while the systems and methods disclosed are generally described in the context of spatio-spectral imaging, it will be recognized that the invention encompasses similar measurements in which the degree of imaging is greatly reduced, even to the point where there is a single detector element.

Some embodiments of the invention use multispectral imaging (MSI) of skin to provide information about both the surface and subsurface ("multispectral") characteristics of the skin tissue. In addition to the potential of MSI revealing significant information from below the surface of the skin, the plurality of wavelengths, illumination angles, and optical polarization conditions may yield additional information beyond that available through simple surface reflectance measurements. These multispectral characteristics may be described as "textures" and used with a classification methodology that seeks to find characteristics of the data that are locally consistent (e.g., to determine the identity of an individual). Moreover, the plurality of wavelengths, illumination angles, and optical polarization conditions used in this investigation yields additional information beyond that available through simple surface reflectance measurements More broadly, data collected under a plurality of optical conditions, whether they be collected simultaneously or sequentially, is referred to herein as "multispectral" data. A more complete description of aspects of multispectral data is described in co-pending, commonly assigned U.S. patent application Ser. No. 11/379,945, entitled "MULTISPECTRAL BIOMETRIC SENSORS," filed Apr. 24, 2006, the entire disclosure of which is incorporated herein by reference for all purposes. The distinct optical conditions may include differences in polarization conditions, differences in illumination angle, differences in imaging angle, differences in illumination wavelength, and the like. Spatio-spectral data may thus be considered to be a subset of certain types of multispectral data that includes spatial information, e.g., where the different multispectral illumination conditions are recorded with a detector that provides for at least a pair of measurements at substantially the same illumination condition and different spatial or angular positions. Alternatively, spatio-spectral data may also be derived from a single detector that measures the optical response of the sample at 2 or more illumination conditions that differ by their spatial or angular orientation with respect to the detector. Also, as used herein, "small-area" sensors refers in various embodiments to sensors having an active area less than 1 cm$^2$, with certain specific embodiments using sensors having an active area less than 0.75 cm$^2$, less than 0.5 cm$^2$, less than 0.25 cm$^2$, less than 0.1 cm$^2$, less than 0.05 cm$^2$, or less than 0.01 cm$^2$. In one embodiment, the sensor is substantially a point sensor.

It will be appreciated that the devices, systems, and methods described herein may be applied to many types of biometric identification. Particularly, locally consistent features may be identified in a number of different regions of the body. For example, various volar surfaces of the skin may include locally consistent features which may be identified with small-area sensors according to the invention, including the volar surfaces of the palm, fingers, joints, knuckles, etc. As such, while many embodiments of the invention are described with reference to fingerprints, it will be appreciated that the embodiments may also apply to other biometric sites, and should not be taken as limiting in any way.

There are a number of ways of using texture matching of fingerprints. In one example, a local texture analysis using Gabor filters may be applied to tessellated regions around the core point. In another example, a Fourier analysis fingerprint texture may be used as the basis for biometric determinations. In still another example, wavelet analyses may be applied to fingerprint images to distinguish between them. While these examples differ in basis functions and other methodological matters, they are all based on conventional fingerprint images. In other words, the observed textural pattern is extracted from a single image, which may limit the information content and may be adversely affected by artifacts due to effects such as dry skin, poor contact between the skin and sensor, and other operationally important matters.

Some embodiments of the invention use multiple images taken with a robust form of imaging. The images contain information about both the surface and subsurface characteristics of the skin. In certain embodiments, the data plane in the MSI stack that most closely matches conventional optical fingerprinting images is removed from the texture analysis in order to avoid the presence of spurious effects (e.g., dry skin, poor contact between the skin site and the sensor platen, etc.).

It will be appreciated that there are a number of ways to perform biometric matching using small-area fingerprint sensors. One approach may be to build up a large enrollment image by piecing together a series of small fingerprint images taken over multiple placements of the finger (known as "mosaiking"). Another approach may be to combine minutiae information instead of combining the images themselves. One limitation to these approaches is that they may require precise enrollment of a skin site to take accurate measurements. For example, to provide accurate results with these types of sensors, a user may have to precisely locate his finger on the sensor, avoid any movements of the skin during measurement, etc.

As such, it may be desirable instead to sense small-area features of the skin site that are locally consistent over other areas of the skin site. Some embodiments of the invention find characteristics of the skin site that are locally consistent. Using locally consistent characteristics may allow an enrollment measurement to be made at one skin site and successfully verified at a different (e.g., nearby) skin site. This may minimize certain types of errors inherent in many small-area sensors (e.g., slight movements of the skin site during sensing, etc.) and may improve usability and reliability.

To capture information-rich data about the surface and subsurface features of a skin site (e.g., the skin of a finger), an MSI sensor may collect multiple images of the skin site under a variety of optical conditions. The raw images may be captured using different wavelengths of illumination light, different polarization conditions, and/or different illumination orientations. Each raw image may then contain somewhat different, but complementary, information about the skin site. The different wavelengths may penetrate the skin to different depths and be absorbed and scattered differently by various chemical components and structures in the skin. The different polarization conditions may change the degree of contribution of surface and subsurface features to the raw image. Further, different illumination orientations may change the location and degree to which surface features are accentuated.

Embodiments of the MSI sensors according to the invention are configured to detect textural information from a skin site. "Texture" may generally refer to any of a large number of metrics that describe some aspect of a spatial distribution of tonal characteristics of an image, some of which were described above. For example, some textures, such as those commonly found in fingerprint patterns or wood grain, are flowlike and may be well described by metrics such as an orientation and coherence. For textures that have a spatial regularity (at least locally), certain characteristics of the Fourier transform and the associated power spectrum are important such as energy compactness, dominant frequencies and orientations, etc. Certain statistical moments such as mean, variance, skew, and kurtosis may be used to describe texture. Moment invariants may be used, which are combinations of various moments that are invariant to changes in scale, rotation, and other perturbations. Gray-tone spatial dependence matrices may be generated and analyzed to describe image texture. The entropy over an image region may be calculated as a measure of image texture. Various types of wavelet transforms may be used to describe aspects of the image texture. As mentioned above, steerable pyramids, Gabor filters, and other mechanisms of using spatially bounded basis functions may be used to describe the image texture. These and other such measures of texture known to one familiar in the art may be used individually or in combination in embodiments of the invention.

Image texture may thus be manifested by variations in pixel intensities across an image, which may be used in embodiments of the invention to perform biometric functions. In some embodiments, additional information may be extracted when such textural analysis is performed for different spectral images recorded under different illumination wavelengths and/or polarization conditions and extracted from a multispectral data set, producing a chromatic textural description of the skin site. These embodiments may enable biometric functions to be performed by capturing only a small-area portion of an image of a skin site. The texture characteristics of the skin site are expected to be approximately consistent over the skin site, permitting biometric functions to be performed with measurements made at different portions of the image site. In many instances, it may not even be required that the portions of the skin site used in different measurements overlap with each other.

Exemplary Sensor Embodiments

This ability to use different portions of the skin site provides considerable flexibility in the structural designs that may be used. This is, in part, a consequence of the fact that biometric matching may be performed statistically instead of requiring a match to a deterministic spatial pattern. The sensor may be configured in a compact manner because it need not acquire an image over a specified spatial area. The ability to provide a small sensor also permits the sensor to be made more economically than sensors that need to collect complete spatial information to perform a biometric function. In different embodiments, biometric functions may be performed with purely spectral information, while in other embodiments, spatio-spectral information is used.

FIG. 1 shows a simplified perspective view of an embodiment of an exemplary small-area sensor, according to some embodiments of the present invention. The sensor assembly 100 consists of a series or plurality of light sources 104 arranged in a selected manner on a sensor head 102, which also contains one or more detectors 106. The sensor assembly 100 may also include power conditioning electronics (not shown), which supply power to the light sources 104 and may also include signal processing electronics (not shown) which amplify the resulting signal from the detector 106. A multi-conductor cable 108 may be provided to power the sensor head and to communicate with a system (e.g., a microprocessor or computer) for processing the detected signals.

The light sources 104 may be light emitting diodes (LEDs), laser diodes, vertical cavity surface emitting lasers (VC-SELS), quartz tungsten halogen incandescent bulbs with or without optical pass-band filters and with or without optical shutters, or a variety of other optical sources known in the art. The light sources 104 may each have the same wavelength characteristics or can be comprised of sources with different center wavelengths in the spectral range from about 350 nm to about 2500 nm. In general, the collection of light sources 104 may include some sources that have the same wavelengths as others and some sources that are different. In one embodiment, the light sources 104 include sets of LEDs, laser diodes, VCSELs, or other solid-state optoelectronic devices with differing wavelength characteristics that lie within the spectral range from about 350 nm to about 1100 nm. In some cases, the detector array may include an optical filter array to limit the wavelengths of light seen by certain array elements.

The detector 106 may be a single element or it may be a one- or two-dimensional array of elements. The detector type and material are chosen to be appropriate to the source wavelengths and the measurement signal and timing requirements. For example, the detectors may include PbS, PbSe, InSb, InGaAs, MCT, bolometers and/or micro-bolometer arrays. In one embodiment where the light sources 104 are solid-state optoelectronic devices operating in the spectral range from about 350 nm to about 1100 nm, the detector material is silicon.

The light sources 104 may be sequentially illuminated and extinguished to measure the tissue properties for each source by turning power to each of them on and off. Alternatively, multiple light sources 104 may be electronically modulated using encoding methods that may be known in the art. These encoding patterns include, for example, Fourier intensity modulation, Hadamard modulation, random modulation, and other modulation methods.

It is worth noting that the configuration shown in FIG. 1 includes a number of light sources 104 and a single detector 106, effectively providing variable source-detector spacings. This configuration may be applicable, for example, where a small number of light sources 104 with different wavelength characteristics are available. In these cases, providing variable source-detector spacings may be useful in gathering additional optical information from tissue.

Figure 2:
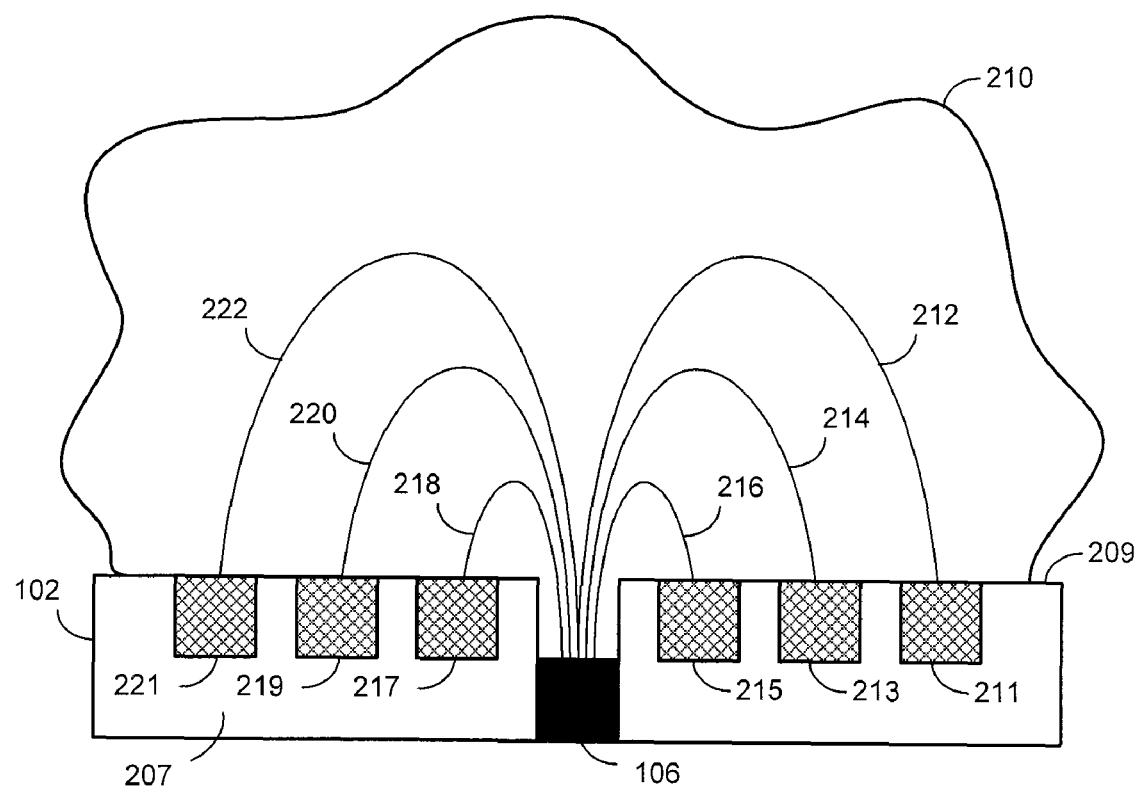
FIG. 2 shows a simplified cross-sectional view of a sensor head, like the sensor head shown in FIG. 1, according to various embodiments of the invention.

FIG. 2 shows a simplified cross-sectional view of a sensor head, like the sensor head 100 shown in FIG. 1, according to some embodiments of the invention. Also shown is the tissue 210 in contact with the face 209 of the sensor head 102 and the mean optical paths 212, 214, 216, 218, 220, and 222 of the light traveling from each light source 211, 213, 215, 217, 219, and 221, respectively, to the detector 106. In acquiring tissue spectral data, measurements can be made in at least two different sampling modes. The optical geometry illustrated in FIG. 2 is known as diffuse reflectance sampling geometry where the light sources and detector lie on the same side of the tissue. An alternative method is known as transmission sampling, wherein light enters a thin tissue region such as an earlobe or a fingertip on one side and then is detected by a detector located on the other side of the tissue. Although light in such regions as the silicon-region can penetrate tissue to significant depths of one centimeter or more, depending upon the wavelength, transmission sampling of the tissue limits the region of the body that can be used. Thus, while either mode of sampling may be applicable to the present invention, and especially to analysis utilizing light in the silicon-region, many embodiments utilize sampling methods based on reflected light.

Referring to FIG. 2, when the tissue is illuminated by a particular light source 211, the resulting signal detected by detector 106 contains information about the tissue optical properties along a path between the source 211 and detector 106. The actual path of any given photon may be highly erratic due to effects of optical scattering by the tissue, but the mean optical path 212 may be a more regular and smooth curve, as shown in the Figure.

The mean optical path (e.g., 212) may, in general, be different for different source-detector separation differences. If another light source 221 is located at the same distance from the detector 106 as light source 211, and the two light sources have the same wavelength characteristics, the resulting signals may be combined (e.g., to increase the resulting signal-to-noise ratio of the measurement) or may be used as independent spatio-spectral measurements. If light source 221 has a different wavelength characteristic from light source 211, the resulting signals may provide information about optical properties of the tissue 210, especially as they relate to biometric determinations, and should be analyzed as distinct data points. In a similar manner, if two light sources have the same wavelength characteristics and are positioned at different distances from the detector 106 (for example light sources 211 and 213), then the resulting information in the two signals is different and the measurements may be recorded and analyzed as distinct data points. Differences in both wavelength characteristics and source-detector separation may provide additional information about optical characteristics of the tissue 210.

In some embodiments, the detector 106 is located either in the center of the sensor head 102 or offset to one side of the sensor head 102 (e.g., to provide for varying source-detector separation distances). The sensor head 102 may be various shapes including oval, square, or rectangular. The sensor head 102 may also have a compound curvature on the optical surface to match the profile of the device in which it is mounted, or to match the profile of the skin site intended to touch the sensor.

Light that reflects from the topmost layer of skin may not contain significant information about the deeper tissue properties. In fact, reflections from the top surface of tissue (known as "specular" or "shunted" light) may sometimes be detrimental to optical measurements. For this reason, FIG. 2 illustrates a sensor head 102 geometry wherein the detector 106 is recessed from the sensor surface 209 in optically opaque material 207 that makes up the body of the sensor head 102. The recessed placement of detector 106 minimizes the amount of light that can be detected after reflecting off the first (e.g., epidermal) surface of the tissue. It can be seen that the same optical blocking effect may be produced by recessing each of the light sources 211, 213, 215, 217, 219, and 221, and/or the detector 106. Of course, other optical blocking methods, such as the use of different polarization filters, are possible according to the invention.

Figure 3:
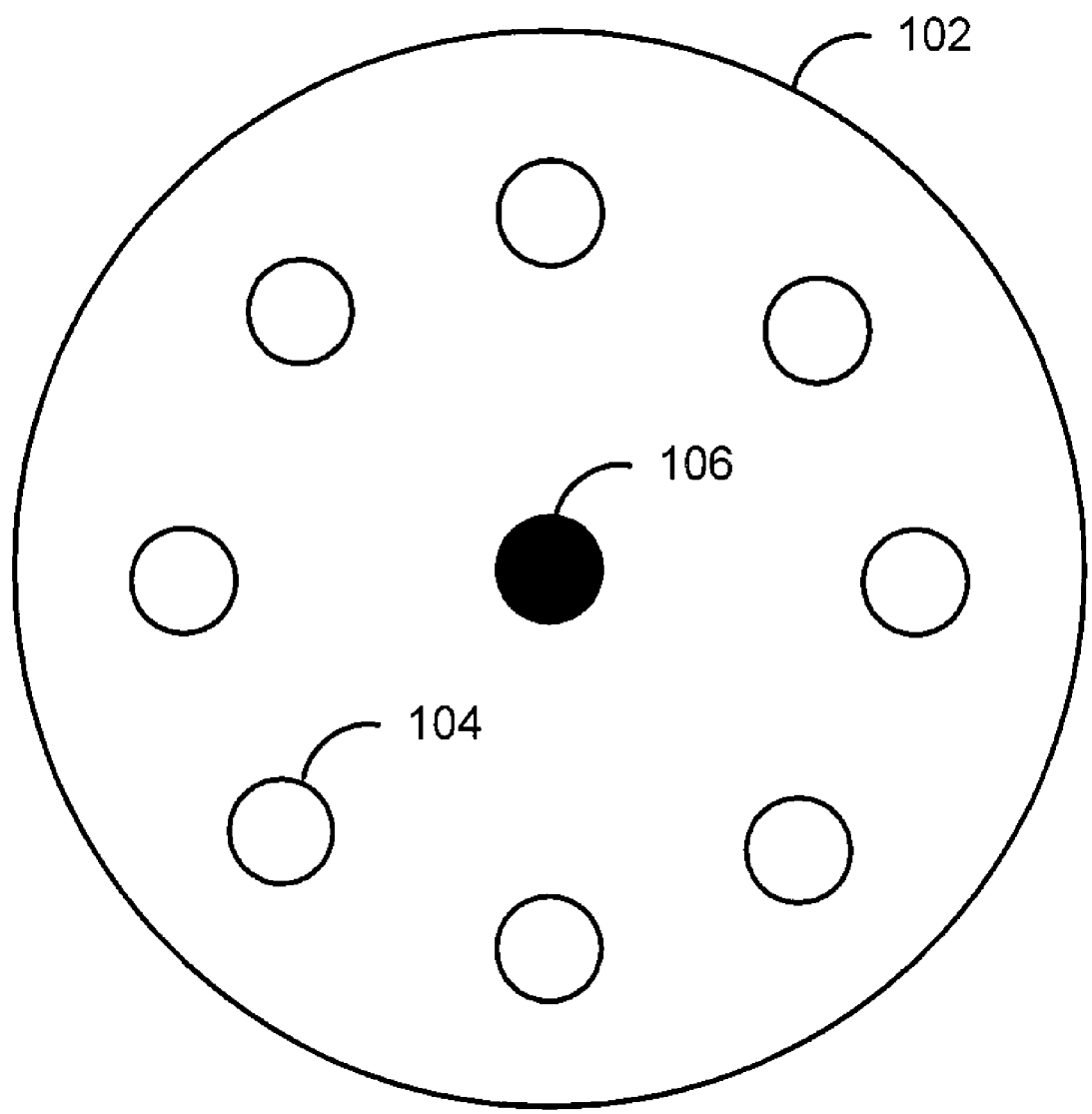
FIG. 3 shows a simplified top view of a sensor head having a number of light sources arranged to be equidistant from a detector, according to various embodiments of the invention.

It will be appreciated that many other configurations of light sources and detectors are possible without departing from the invention. In one embodiment, as shown in FIG. 3, a sensor head 102 has a number of light sources 104 arranged to be equidistant from a detector 106. This configuration may be useful, for example, where each light source 104 is a different wavelength and sufficient light sources 104 may be obtained to achieve desired accuracy results from the system. An example of this may occur where individual light sources result from combining optical filters with one or more broadband (e.g., incandescent) light sources. In this case, many unique wavelength bands may be defined and each of the sources 104 may be placed equidistant from the central detector 106. Alternatively, each of the light sources 104 may be substantially the same and the resulting set of measurements are used as a measure of the spatial differences of the skin at a particular wavelength.

Figure 4:
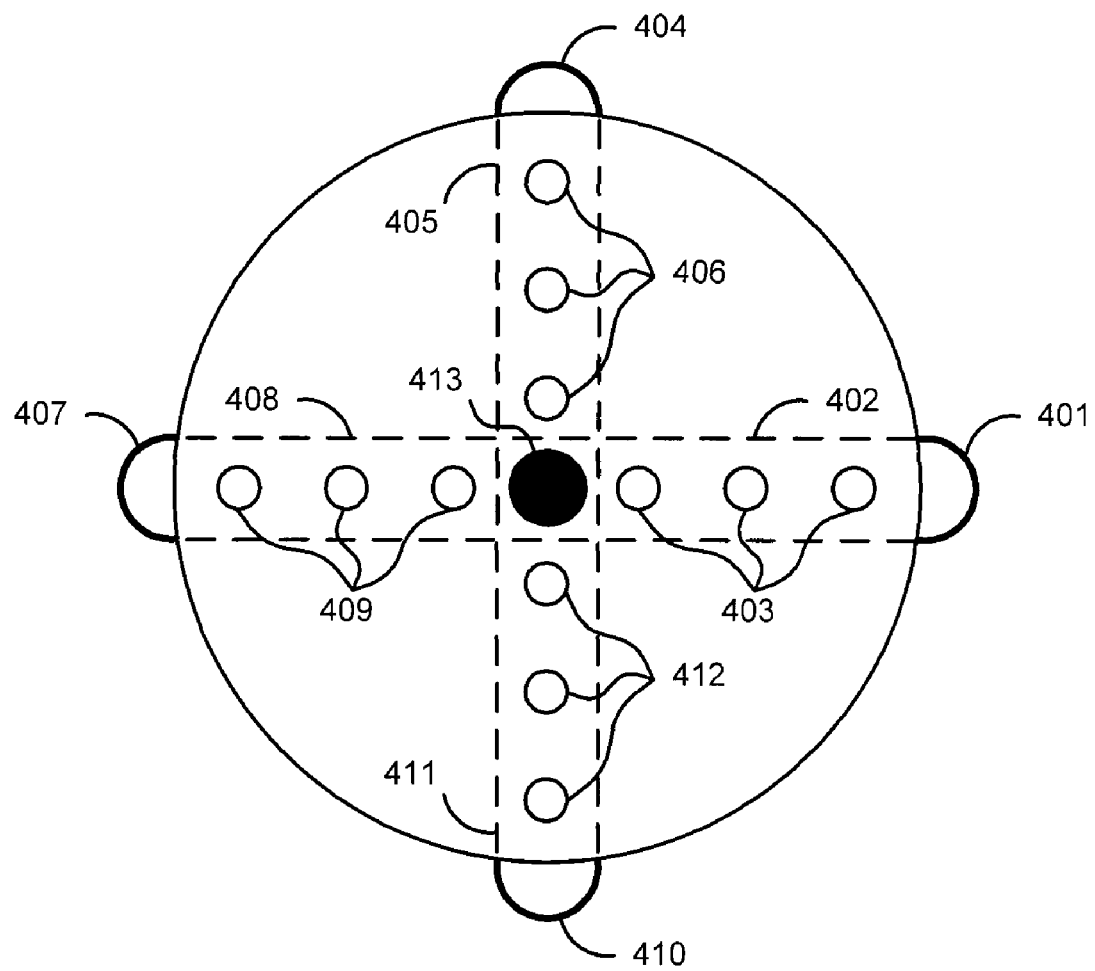
FIG. 4 shows a simplified top view of a sensor head having a number of light sources arranged around a common detector, according to various embodiments of the invention.

In another embodiment, as shown in FIG. 4, a number of light sources 401, 404, 407, 410 are arranged around a common detector 413. Four different light sources 401, 404, 407, 410 are shown for illustration but fewer or more can be used in a particular embodiment. Each of the light sources 401, 404, 407, 410 is optically coupled to a different optical waveguide 402, 405, 408, 411. Each waveguide 402, 405, 408, 411 has individually controllable electronic or mechanical optical shutters 403, 406, 409, 412. These optical shutters 403, 406, 409, 412 can be individually controlled to encode the light by allowing light to enter the tissue from a waveguide 402, 405, 408, 411 at a predetermined position or positions. In certain embodiments, the optical shutters 403, 406, 409, 412 include micro-electromechanical systems ("MEMS") structures. The light sources 401, 404, 407, 410 may include different LEDs, laser diodes, VCSELs, or other types of illumination sources. Alternatively, one or more incandescent sources with different optical filters may be used to generate light of different wavelength characteristics to couple into each of the waveguides 402, 405, 408, 411.

Figure 5:
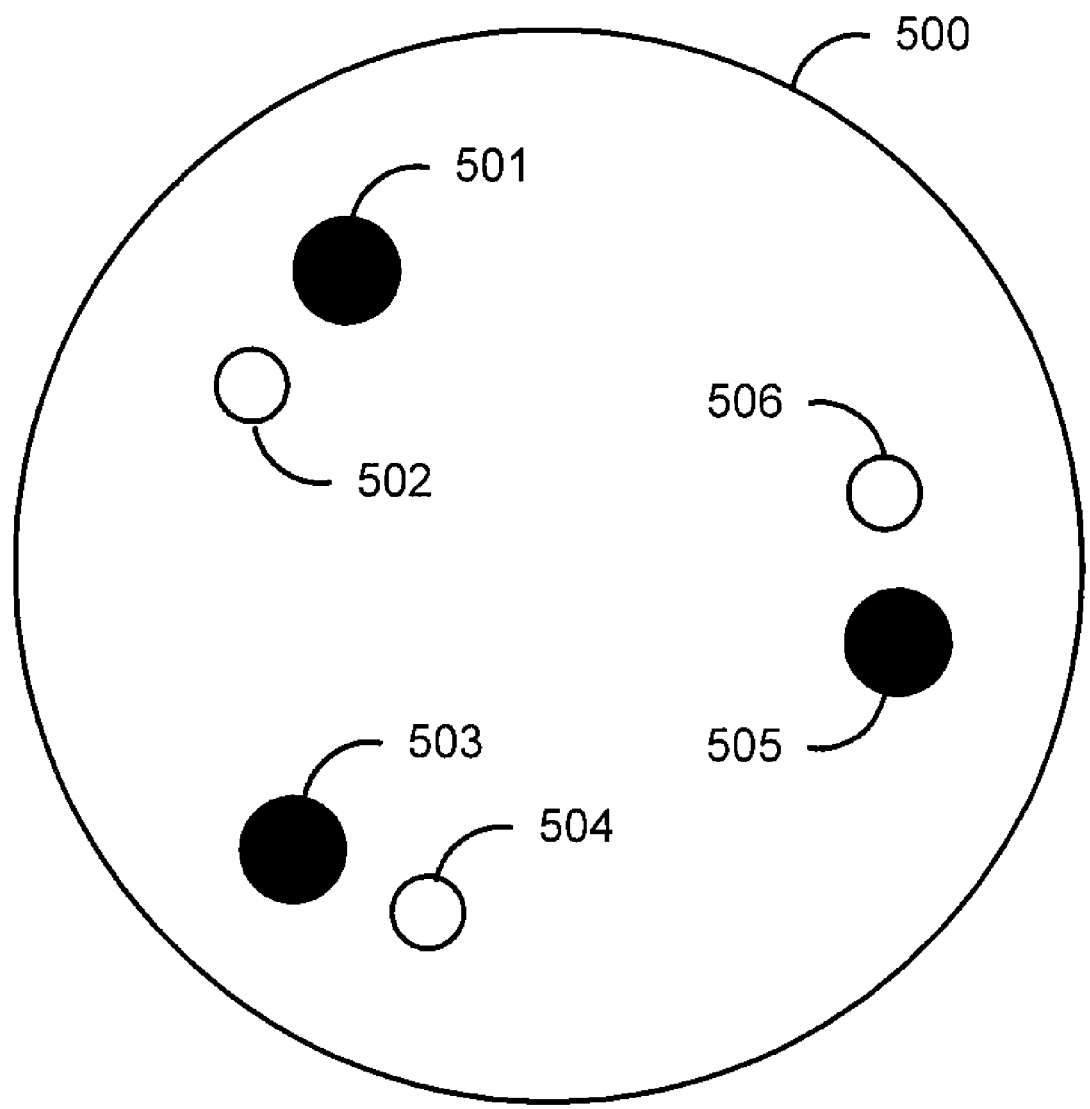
FIG. 5 shows a simplified top view of a sensor head having a number of light sources arranged with respect to multiple detector elements, according to various embodiments of the invention.

In yet another embodiment, multiple source-detector distances may be achieved by using more than one detector element, as shown in FIG. 5. In the illustrated embodiment, each of three different light sources 502, 504, 506 is positioned relative to three detectors 501, 503, 505 such that the spacing between a given light source and each of the detectors is different. For example, the source-detector spacing for a light source 502 is shortest with respect to detector 501 and longest with respect to detector 505. By turning on the light sources 502, 504, 506 in a sequential or encoded pattern and measuring the response at each of the three detectors 501, 503, 505, tissue characteristics for some or all of the available source-detector separations at some or all of the wavelengths may be measured.

Figure 6:
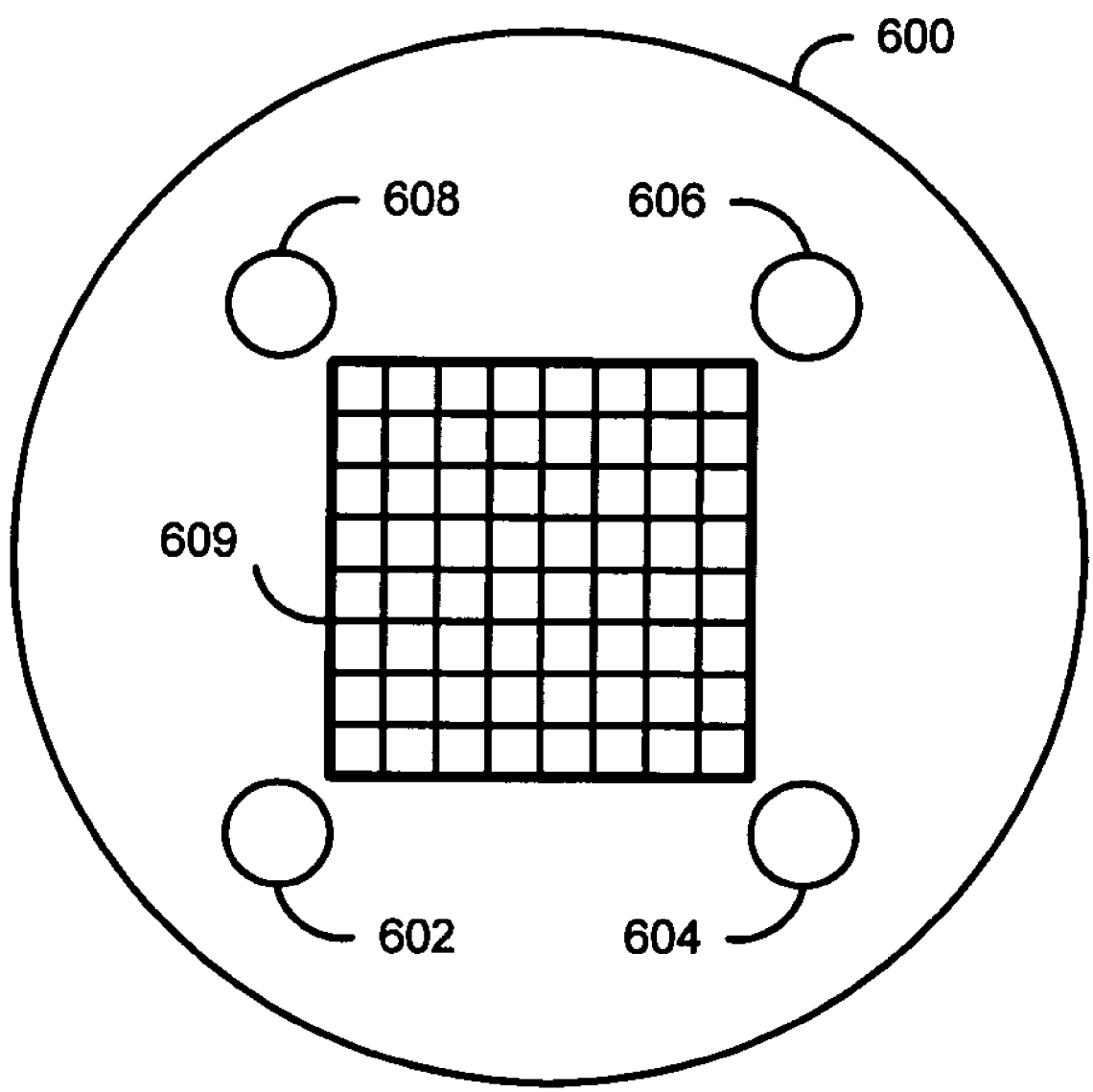
FIG. 6 shows a simplified top view of a sensor head having a number of light sources arranged around a detector array, according to various embodiments of the invention.

Some embodiments configure multiple detector elements and multiple illumination sources using a detector array. FIG. 6 illustrates a simplified top view of a sensor 600 using a detector array according to some embodiments of the invention. In this embodiment, multiple light sources 602, 604, 606, 608 are placed at the perimeter of a detector array 609. The signal detected at each of the array elements may then represent a different source-detector separation with respect to the light from a given light source. Many variants on this configuration may exist, including the use of one dimensional ("1-D"), two-dimensional ("2-D"), or three-dimensional ("3-D") arrays, and placing sources within the array as well as on the periphery.

Other embodiments are configured differently to detect similar or different optical data. For example, many different types of multi-spectral imaging ("MSI") sensors are possible. One embodiment of an MSI biometric sensor is depicted with the schematic diagram of FIG. 7, which shows a front view of the MSI sensor using direct illumination. The MSI biometric sensor 701 comprises an illumination subsystem 721 having one or more light sources 703 and a detection subsystem 723 with an imager 715. The figure depicts an embodiment in which the illumination subsystem 721 comprises a plurality of illumination subsystems 721*a* and 721*b*, but the invention is not limited by the number of illumination subsystems 721 or detection subsystems 723. For example, the number of illumination subsystems 721 may conveniently be selected to achieve certain levels of illumination, to meet packaging requirements, and to meet other structural constraints of the MSI biometric sensor 701.

Illumination light passes from the source 703 through illumination optics 705 that shape the illumination to a desired form, such as in the form of flood light, light lines, light points, and the like. The illumination optics 705 are shown for convenience as consisting of a lens but may more generally include any combination of one or more lenses, one or more mirrors, and/or other optical elements. The illumination optics 705 may also comprise a scanner mechanism (not shown) to scan the illumination light in a specified one-dimensional, or two-dimensional, or three-dimensional pattern. The light source 703 may comprise a point source, a line source, an area source, or may comprise a series of such sources in different embodiments. In various embodiments, one or more light sources 703 may be configured to illuminate a skin site 719 (e.g., the skin of a finger) at different wavelengths, different polarization conditions, and/or different illumination orientations.

In some embodiments, the light source 703 may comprise one or more quasimonochromatic sources in which the light is provided over a narrow wavelength band. Such quasimonochromatic sources may include such devices as light-emitting diodes, laser diodes, or quantum-dot lasers. Alternatively, the light source 703 may comprise a broadband source such as a white-light LED, an incandescent bulb, or a glow bar. In the case of a broadband source, the illumination light may pass through a bandpass filter 709 to narrow the spectral width of the illumination light. In one embodiment, the bandpass filter 709 comprises one or more discrete optical bandpass filters. In another embodiment, the bandpass filter 709 comprises a continuously variable filter that moves rotationally or linearly (or with a combination of rotational and linear movement) to change the wavelength of illumination light. In still another embodiment, the bandpass filter 709 comprises a tunable filter element such as a liquid-crystal tunable filter, an acousto-optical tunable filter, a tunable Fabry-Perot filter, or other filter mechanism known to one knowledgeable in the art.

In other embodiments, white light is used. As used herein, "white light" refers to light that has a spectral composition amenable to separation into constituent wavelength bands, which in some cases may comprise primary colors. The usual primary colors used to define white light are red, green, and blue, but other combinations may be used in other instances, as will be known to those of skill in the art. For clarity, it is emphasized that "white light" as used herein might not appear white to a human observer and might have a distinct tint or color associated with it because of the exact wavelength distribution and intensity of the constituent wavelength bands. In other cases, the white light may comprise one or more bands in the ultraviolet or infrared spectral regions. In some cases, the white light might not even be visible at all to a human observer when it consists of wavelength bands in the infrared and/or ultraviolet spectral regions. A portion of the light scattered by the skin and/or underlying tissue exits the skin and is used to form an image of the structure of the tissue at and below the surface of the skin. Because of the wavelength-dependent properties of the skin, the image formed from each wavelength of light comprised by the white light may be different from images formed at other wavelengths. In some embodiments, an optical filter or filter array may be incorporated with the detector array to separate the white light into a set constituent wavelengths. For example a color filter array comprised of red, green and blue filter elements arranged in a Bayer pattern may be used to separate the white light, as known to one familiar in the art.

Various embodiments of the illumination subsystem 721 and detection subsystem 723 are configured to operate in a variety of optical regimes and at a variety of wavelengths. One embodiment uses light sources 703 that emit light substantially in the region of 350-1100 nanometers. In this embodiment, the detector 715 may be based on silicon detector elements or other detector material known to those of skill in the art as sensitive to light at such wavelengths. In another embodiment, the light sources 703 may emit radiation at wavelengths that include the near-infrared regime of 1.0-2.5 microns, in which case the detector 715 may include elements made from InGaAs, InSb, PbS, MCT, and other materials known to those of skill in the art as sensitive to light at such wavelengths.

Figure 7:
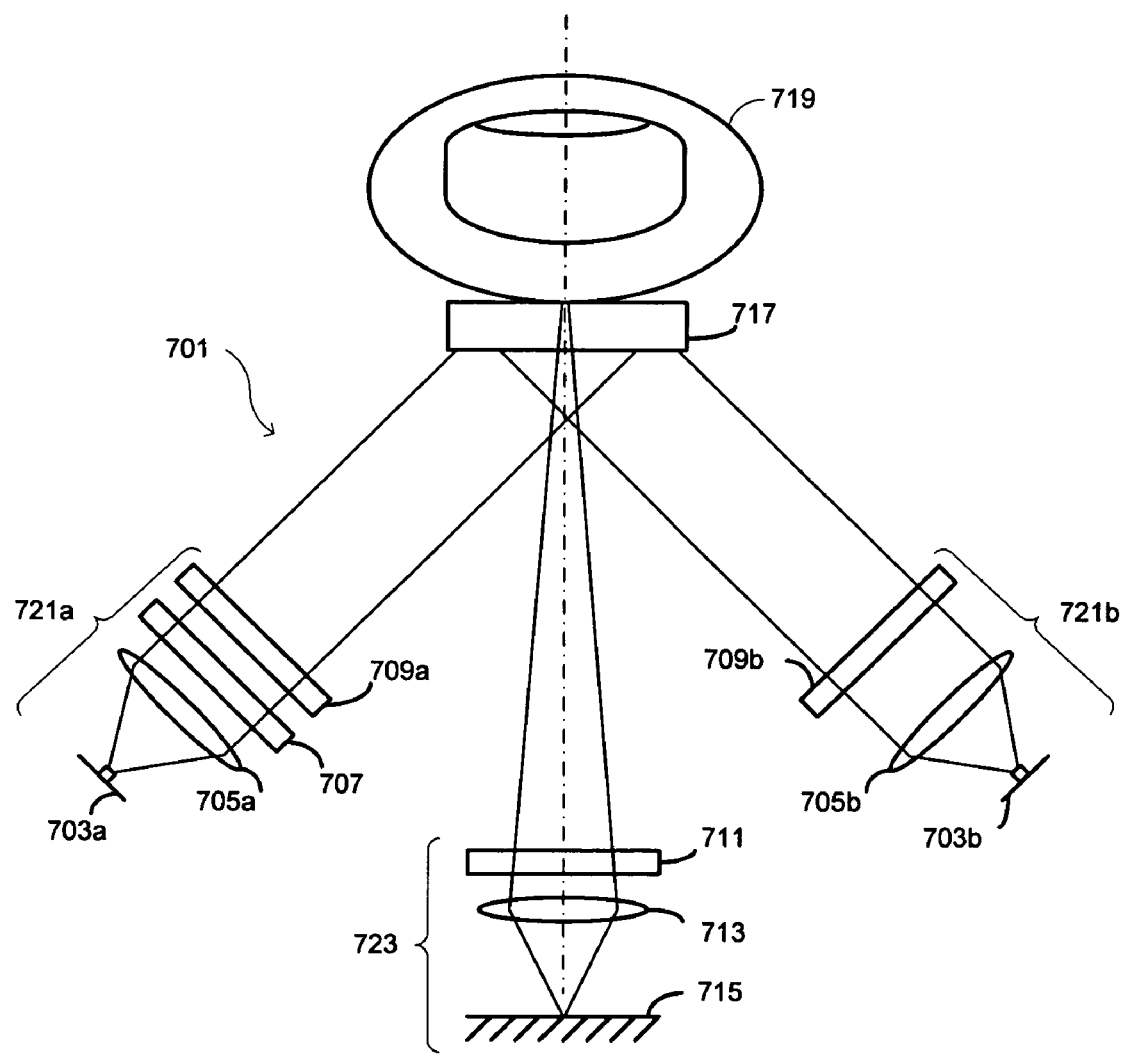
FIG. 7 shows a simplified illustration of an embodiment of a multi-spectral biometric sensor using direct illumination, according to various embodiments of the invention.

In the embodiment shown in FIG. 7, the first illumination subsystem 721*a* includes a first light emitting diode ("LED") 703*a* (i.e., the light source) and an illumination polarizer 707. Light from the first LED 703*a* passes through the illumination polarizer 707 before illuminating a finger 719 (i.e., the skin site) as it rests on a sensor platen 717. The illumination polarizer 707 may include, for example, a linear polarizer or a circular polarizer. Light interacts with the finger 719 and a portion of the light is directed toward the detection subsystem 723. Other light which does not reflect directly back toward the detection subsystem 723 may undergo refractions, scattering, other reflections, and other optical events. Some of this other light may ultimately reflect toward the detection subsystem 723.

The detection subsystem 723 includes an imaging polarizer 711. The imaging polarizer 711 is oriented with its optical axis to be orthogonal to the axis of the illumination polarizer 707, such that light with the same polarization as the illumination light is substantially attenuated by the imaging polarizer 711. This may significantly reduce the influence of light reflected from the surface of the skin and emphasize light that has undergone multiple optical scattering events after penetrating the skin.

The second illumination subsystem 721b includes a second LED 703b, but no illumination polarizer 707. When the second LED 703b is illuminated, the illumination light may be randomly polarized. The surface-reflected light and the deeply penetrating light may both able to pass through the imaging polarizer 711 in equal proportions due to the random polarization. As such, the image produced from this unpolarized second LED 703b may contain stronger influence from surface features of the finger.

It is worth noting that the direct-illumination sources, the polarized first LED 703a and the unpolarized second LED 703b, as well as the imaging system, may be arranged to avoid critical-angle phenomena at platen-air interfaces. This may provide certainty that each illuminator will illuminate the finger 719 and that the imager 715 will image the finger 719 (e.g., regardless of whether the skin is dry, dirty, or even in good contact with the sensor).

In some embodiments, the sensor layout and components may advantageously be selected to minimize the direct reflection of the illumination into the detection optics 713. In one embodiment, such direct reflections are reduced by relatively orienting the illumination subsystem 721 and detection subsystem 723 such that the amount of directly reflected light detected is minimized. For instance, optical axes of the illumination subsystem 721 and the detection subsystem 723 may be placed at angles such that a mirror placed on the platen 717 does not direct an appreciable amount of illumination light into the detection subsystem 723. In addition, the optical axes of the illumination and detection subsystems 721 and 723 may be placed at angles relative to the platen 717 such that the angular acceptance of both subsystems is less than the critical angle of the system; such a configuration avoids appreciable effects due to total internal reflectance ("TIR") between the platen 717 and the skin site 719.

In other embodiments, the detection subsystem 723 may incorporate detection optics that include lenses, mirrors, and/or other optical elements that form an image of the region near the platen surface 717 onto the detector 715. The detection optics 713 may also include a scanning mechanism (not shown) to relay portions of the platen region onto the detector 715 in sequence. It will be appreciated that there are many ways to configure the detection subsystem 723 to be sensitive to light that has penetrated the surface of the skin and undergone optical scattering within the skin and/or underlying tissue before exiting the skin.

Figure 8:
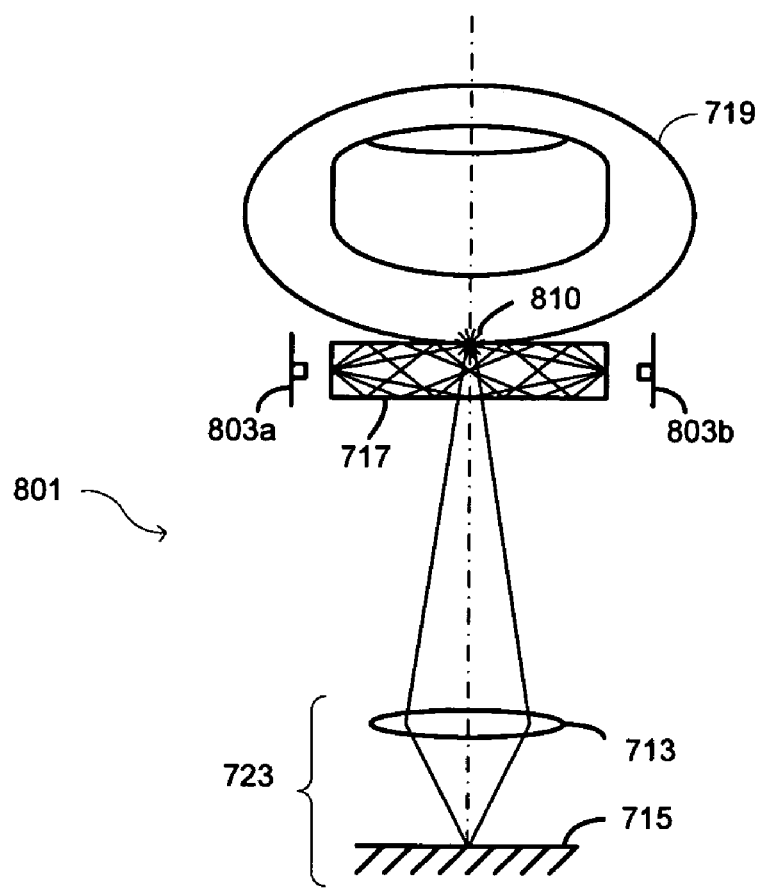
FIG. 8 shows a simplified illustration of an embodiment of a multi-spectral biometric sensor using TIR imaging, according to various embodiments of the invention.

In some embodiments, in addition to or instead of the direct illumination illustrated in FIG. 7, the MSI sensor 701 also integrates a form of TIR imaging. For example, the polarization effects discussed with respect to FIG. 7 may be effective when non-contact sensors are used, while TIR and other techniques may be more effective with contact sensors. FIG. 8 provides an exemplary illustration of an MSI sensor 801 using TIR imaging. Like the direct-illumination MSI sensor 701 (FIG. 7), the TIR-based MSI sensor 801 includes one or more light sources 803 and a detection subsystem 723 with an imager 715.

In the TIR illumination mode, one or more light sources 803 (e.g., LEDs) illuminate the side of the platen 717. A portion of the illumination light propagates through the platen 717 by making multiple TIR reflections at the platen-air interfaces. At points where the TIR is broken by contact with the skin (e.g., 810), light enters the skin and is diffusely reflected. A portion of this diffusely reflected light is directed toward the imaging system and passes through the imaging polarizer (since this light is randomly polarized), forming an image for this illumination state. Unlike all the direct illumination states, the quality of the resulting raw TIR image may be dependent on having skin of sufficient moisture content and cleanliness making good optical contact with the platen, just as is the case with conventional TIR sensors.

In practice, many MSI sensors may contain multiple direct-illumination LEDs of different wavelengths. For example, the Lumidigm J110 MSI sensor has four direct-illumination wavelength bands (430, 530, and 630 nanometers, as well as a white light), in both polarized and unpolarized configurations. When a finger is placed on the sensor platen, eight direct-illumination images are captured along with a single TIR image. The raw images are captured on a 640×480 image array with a pixel resolution of 525 ppi. All nine images are captured in approximately 500 mSec.

Figure 9A:
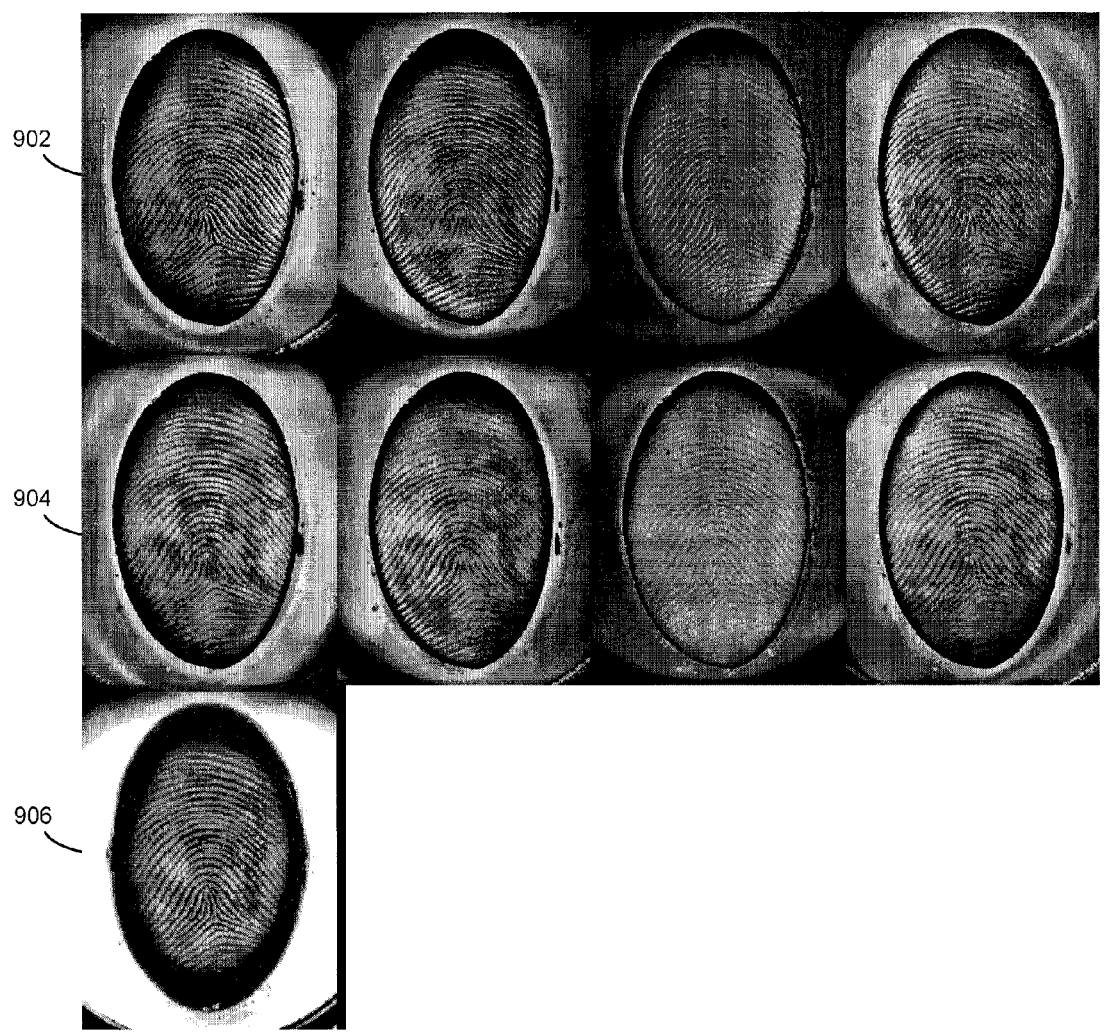
FIG. 9A illustrates nine exemplary images captured during a single finger placement using an embodiment of an MSI biometric sensor, according to various embodiments of the invention.

FIG. 9A illustrates nine exemplary images captured during a single finger placement using an embodiment of an MSI biometric sensor. The upper row 902 shows raw images for unpolarized illumination wavelengths of blue (430 nanometers), green (530 nanometers), and red (630 nanometers), as well as white light. The middle row 904 shows images, corresponding to those in the upper row 902, for a cross-polarized case. The single image on the bottom row 906 shows a TIR image. The grayscale for each of the raw images has been expanded to emphasize the features.

It can be seen from FIG. 9 that there are a number of features present in the raw data including the textural characteristics of the subsurface skin, which appear as mottling that is particularly pronounced under blue and green illumination wavelengths. As well, the relative intensities of the raw images under each of the illumination conditions is very indicative of the spectral characteristics (e.g., color) of the finger or other sample. It is worth noting that the relative intensities have been obscured in FIG. 9 to better show the comparative details of the raw images.

The set of raw images shown in FIG. 9 may be combined together to produce a single representation of the fingerprint pattern. In some embodiments, this fingerprint generation relies on a wavelet-based method of image fusion to extract, combine, and enhance those features that are characteristic of a fingerprint. In one embodiment, the wavelet decomposition method that is used is based on the dual-tree complex wavelet transform ("DTCWT"). Image fusion may occur by selecting and compiling the coefficients with the maximum absolute magnitude in the image at each position and decomposition level.

Figure 9B:
FIG. 9B shows an exemplary result of applying a compositing algorithm to two placements of the same finger, according to various embodiments of the invention.

An inverse wavelet transform may then be performed on the resulting collection of coefficients, yielding a single, composite image. An example of the result of applying the compositing algorithm to two placements of the same finger is shown in FIG. 9B. The two composite fingerprint images (*0952 and 954) may then be used with conventional fingerprint matching software.

In some embodiments, the DTCWT process used to generate composite fingerprint images is also used to provide the spectral-textural features of the multispectral data. In one embodiment, the coefficients from a 3rd level of the DTCWT decomposition of the multispectral image stack are used as features for the texture analysis. Since the strength and quality of the raw TIR image plane may be highly variable (dependent on skin moisture, good contact, etc), certain embodiments omit the TIR image plane from the multispectral texture analysis.

In some embodiments, an inter-image product, P, is defined as the conjugate product of coefficients at some direction, d, and decomposition level, k, generated by any two of the raw multispectral images, i and j, in a multispectral image stack at location x,y, as defined by:

$$P_{i,j}(x,y,d,k) = C_i(x,y,k) C_j^*(x,y,k).$$

In this equation, $C_i(x,y,k)$ is the complex coefficient for image i at decomposition level k, direction d, and location x,y, and $C_j^*(x,y,k)$ is the conjugate of the corresponding complex value for image j. The conjugate products may represent the fundamental features of the image while remaining insensitive to translation and some amount of rotation.

In one embodiment, all real and imaginary components of all the conjugate products generated from each unique image pair are compiled as a feature vector. For eight raw image planes, this results in a 384-element vector (28 conjugate products per direction, six directions, two scalar values (i.e., real and imaginary) per product for i≠j; plus eight conjugate products per direction, six directions, one scalar value (i.e., real only) for i=j). In addition, the isotropic magnitudes of the coefficients are added to the feature vector, where the isotropic magnitude is the sum of the absolute magnitudes over the six directional coefficients. Finally, the mean DC values of each of the raw images over the region of analysis are added to the feature vector. Concatenating all of these values results in a 400-element feature vector at each element location.

In addition to the direct illumination and TIR sensors of FIGS. 7 and 8, respectively, some embodiments of MSI sensors use illuminated arrays. FIG. 10A shows an illustration of an exemplary embodiment of an array-based MSI sensor. The sensor 1000 includes a number of light sources 1004 and an imager 1008. In some embodiments, the light sources 1004 include white-light sources, although in other embodiments, the light sources 1004 include quasi-monochromatic sources. Similarly, the imager 1008 may include a monochromatic or color imager.

Figure 11A:
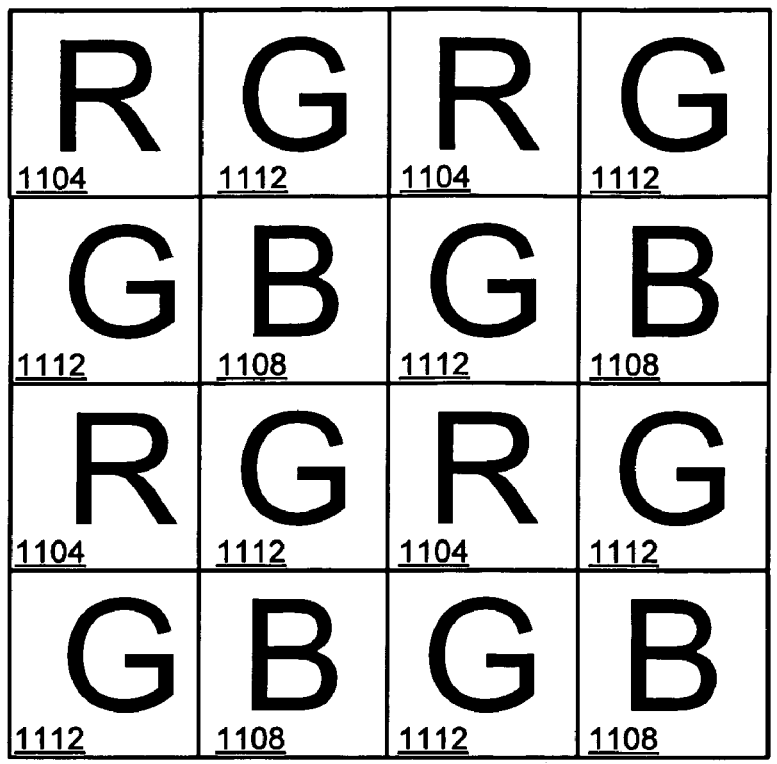
FIG. 11A shows an illustration of an exemplary Bayer color filter array in which filter elements correspond to a set of primary colors and are arranged in a Bayer pattern.

In one example, the imager 1008 has a Bayer color filter array in which filter elements corresponding to a set of primary colors are arranged in a Bayer pattern. An example of such a pattern is shown in FIG. 11A for an arrangement that uses red 1104, green 1112, and blue 1108 color filter elements. In some instances, the imager 1008 may additionally include an infrared filter or other filter, e.g., disposed to reduce the amount of infrared light detected.

Figure 11B:
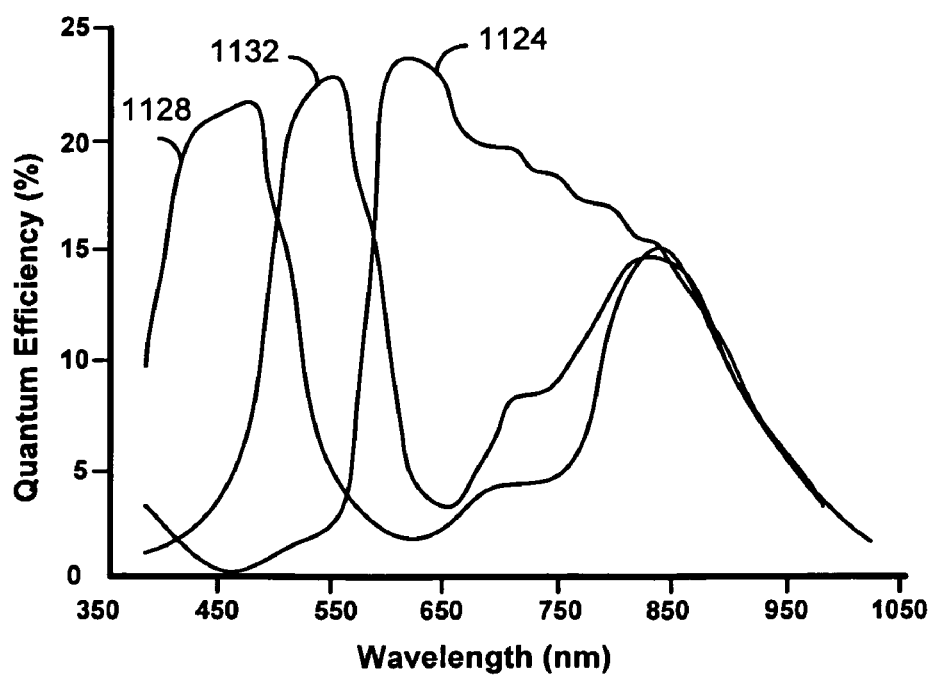
FIG. 11B shows an illustrative color response curve for an exemplary Bayer filter, like the one in FIG. 11A.

FIG. 11B shows an illustrative color response curve for an exemplary Bayer filter. As shown, there may generally be some overlap in the spectral ranges of the red 1124, green 1132, and blue 1128 transmission characteristics of the filter elements. As evident particularly in the curves for the green 1132 and blue 1128 transmission characteristics, the filter array may allow the transmission of infrared light. This may be avoided with the inclusion of an infrared filter as part of the detector subsystem. In other embodiments, the infrared filter may be omitted and one or more light sources 1004 that emit infrared light may be incorporated. In this way, all color filter elements 1104, 1108, and 1112 may allow the light to substantially pass through, resulting in an infrared image across the entire imager 1008.

Returning to FIG. 10A, in some embodiments, the sensor 1000 is a "contact" sensor, because the image is collected substantially in the region of the skin site 719 being measured. It is possible, however, to have different configurations for operating the sensor, some with the imager 1008 substantially in contact with the skin site 719 and some with the imager 1008 displaced from the region of the skin site 719.

In the embodiment of FIG. 10B, the imager 1008 of the sensor 1000-1 is substantially in contact with the skin site 719. Light from the sources 1004 propagates beneath the tissue of the skin site 719. This may permit light scattered from the skin site 719 and in the underlying tissue to be detected by the imager 1008.

An alternative embodiment in which the imager 1008 is displaced from the skin site 719 is shown schematically in FIG. 10C. In this drawing the sensor 1000-2 includes an optical arrangement 1012 that translates an image at the region of the skin site 719 to the imager 1008. In one embodiment, the optical arrangement 1012 includes a number of optical fibers, which translate individual pixels of an image by total internal reflection along the fiber without substantially loss of intensity. In this way, the light pattern detected by the imager 1008 is substantially the same as the light pattern formed at the region of the skin site 719. The sensor 1000-2 may thus operate in substantially the same fashion as the sensor 1000-1 shown in FIG. 10B. That is, light from the sources 1004 is propagated to the skin site, where it is reflected and scattered by underlying tissue after penetrating the skin site 719. Because information is merely translated substantially without loss, the image formed by the imager 1008 in such an embodiment may be substantially identical to the image that would be formed with an arrangement like that in FIG. 10A.

In embodiments where purely spectral information is used to perform a biometric function, spectral characteristics in the received data may be identified and compared with an enrollment database of spectra. The resultant tissue spectrum of a particular individual includes unique spectral features and combinations of spectral features that can be used to identify individuals once a device has been trained to extract the relevant spectral features. Extraction of relevant spectral features may be performed with a number of different techniques, including linear and quadratic discriminant analysis, genetic algorithms, simulated annealing, and other such techniques. While not readily apparent in visual analysis of a spectral output, such analytical techniques can repeatably extract unique features that can be discriminated to perform a biometric function. Classification may be performed using a variety of methods including support vector machines, K nearest neighbors, neural networks, and other well known classification methods. Examples of specific techniques are disclosed in commonly assigned U.S. Pat. No. 6,560,352, entitled "APPARATUS AND METHOD OF BIOMETRIC IDENTIFICATION OR VERIFICATION OF INDIVIDUALS USING OPTICAL SPECTROSCOPY"; U.S. Pat. No. 6,816,605, entitled "METHODS AND SYSTEMS FOR BIOMETRIC IDENTIFICATION OF INDIVIDUALS USING LINEAR OPTICAL SPECTROSCOPY"; U.S. Pat. No. 6,628,809, entitled "APPARATUS AND METHOD FOR IDENTIFICATION OF INDIVIDUALS BY NEAR-INFRARED SPECTRUM"; U.S. Pat. No. 7,203,345, entitled "APPARATUS AND METHOD FOR IDENTIFICATION OF INDIVIDUAL BY NEAR-INFRARED SPECTRUM," filed Sep. 12, 2003 by Robert K. Rowe et al.; and U.S. patent application Ser. No. 09/874,740, entitled "APPARATUS AND METHOD OF BIOMETRIC DETERMINATION USING SPECIALIZED OPTICAL SPECTROSCOPY SYSTEM," filed Jun. 5, 2001 by Robert K. Rowe et al. The entire disclosure of each of the foregoing patents and patent applications is incorporated herein by reference in its entirety.

Many of the methods taught by the foregoing disclosures are readily applicable to spatio-spectral data. In particular, all or part of the spatio-spectral data may be analyzed using techniques such as wavelets, Fourier decomposition, steerable pyramids, Gabor filters, and other decomposition methods known in the art. The coefficents derived from these decompositions may then be concatenated together into a vector of values as described elsewhere in this disclosure. The resulting vector may then be analyzed in similar ways as a vector of spectral values can be.

The ability to perform biometric functions with image-texture information, including biometric identifications, may exploit the fact that a significant portion of the signal from a living body is due to capillary blood. For example, when the skin site 719 comprises a finger, a known physiological characteristic is that the capillaries in the finger follow the pattern of the external fingerprint ridge structure. Therefore, the contrast of the fingerprint features relative to the illumination wavelength is related to the spectral features of blood. In particular, the contrast of images taken with wavelengths longer than about 580 nanometers may be significantly reduced relative to those images taken with wavelengths less than about 580 nanometers. Fingerprint patterns generated with non-blood pigments and other optical effects (e.g., Fresnel reflectance) may have a different spectral contrast.

Light scattered from a skin site 719 may be subjected to variety of different types of comparative texture analyses in different embodiments. Some embodiments make use of a form of moving-window analysis of image data derived from the collected light to generate a figure of merit, and thereby evaluate the measure of texture or figure of merit. In some embodiments, the moving window operation may be replaced with a block-by-block or tiled analysis. In some embodiments, a single region of the image or the whole image may be analyzed at one time.

In one embodiment, fast-Fourier transforms are performed on one or more regions of the image data. An in-band contrast figure of merit C is generated in such embodiments as the ratio of the average or DC power to in-band power. Specifically, for an index i that corresponds to one of a plurality of wavelengths comprised by the white light, the contrast figure of merit is:

$$C_i \equiv \frac{\sum_\xi \sum_\eta |F_i(\xi,\eta)|^2 \big|_{R_{low}^2 < (\xi^2+\eta^2) < R_{high}^2}}{|F_i(0,0)|^2}.$$

In this expression, $F_i(\xi,\eta)$ is the Fourier transform of the image $f_i(x,y)$ at the wavelength corresponding to index i, where x and y are spatial coordinates for the image. The range defined by $R_{low}$ and $R_{high}$ represents a limit on spatial frequencies of interest for fingerprint features. For example, $R_{low}$ may be approximately 1.5 fringes/mm in one embodiment and $R_{high}$ may be 3.0 fringes/mm. In an alternative formulation, the contrast figure of merit may be defined as the ratio of the integrated power in two different spatial frequency bands. The equation shown above is a specific case where one of the bands comprises only the DC spatial frequency.

In another embodiment, moving-window means and moving-window standard deviations are calculated for the collected body of data and used to generate the figure of merit. In this embodiment, for each wavelength corresponding to index i, the moving-window mean $\mu_I$ and the moving-window standard deviation $\sigma_I$ are calculated from the collected image $f_i(x,y)$. The moving windows for each calculation may be the same size and may conveniently be chosen to span on the order of 2-3 fingerprint ridges. Preferably, the window size is sufficiently large to remove the fingerprint features but sufficiently small to have background variations persist. The figure of merit $C_i$ in this embodiment is calculated as the ratio of the moving-window standard deviation to the moving-window mean:

$$C_i = \frac{\sigma_i}{\mu_i}.$$

In still another embodiment, a similar process is performed but a moving-window range (i.e., max(image values)-min (image values)) is used instead of a moving-window standard deviation. Thus, similar to the previous embodiment, a moving-window mean $\mu_I$ and a moving-window range $\delta_i$ are calculated from the collected image $f_i(x,y)$ for each wavelength corresponding to index i. The window size for calculation of the moving-window mean is again preferably large enough to remove the fingerprint features but small enough to maintain background variations. In some instances, the window size for calculation of the moving-window mean is the same as for calculation of the moving-window range, a suitable value in one embodiment spanning on the order of two to three fingerprint ridges. The figure of merit in this embodiment is calculated as the ratio of the moving-window mean:

$$C_i = \frac{\delta_i}{\mu_i}.$$

This embodiment and the preceding one may be considered to be specific cases of a more general embodiment in which moving-window calculations are performed on the collected data to calculate a moving-window centrality measure and a moving-window variability measure. The specific embodiments illustrate cases in which the centrality measure comprises an unweighted mean, but may more generally comprise any other type of statistical centrality measure such as a weighted mean or median in certain embodiments. Similarly, the specific embodiments illustrate cases in which the variability measure comprises a standard deviation or a range, but may more generally comprise any other type of statistical variability measure such as a median absolute deviation or standard error of the mean in certain embodiments.

In another embodiment that does not use explicit moving-window analysis, a wavelet analysis may be performed on each of the spectral images. In some embodiments, the wavelet analysis may be performed in a way that the resulting coefficients are approximately spatially invariant. This may be accomplished by performing an undecimated wavelet decomposition, applying a dual-tree complex wavelet method, or other methods of the sort. Gabor filters, steerable pyramids and other decompositions of the sort may also be applied to produce similar coefficients. Whatever method of decomposition is chosen, the result is a collection of coefficients that are proportional to the magnitude of the variation corresponding to a particular basis function at a particular position on the image. To perform biometric spoof detection, the wavelet coefficients, or some derived summary thereof, may be compared to the coefficients expected for generated from an appropriate reference dataset samples. In the case where the biometric matching function is a determination of a person's identity, the appropriate reference dataset is one collected from the target person at an earlier time. These enrollment data may be collected from the same skin site or a nearby, locally-consistent skin site and processed in the manner described. The results of the processing are stored in a database and then retrieved to be used to compare to a similar measurement taken at a later time. If the comparison shows that the results are sufficiently close, the sample is deemed match and identity is established or confirmed. Otherwise, the sample is determined not to match (e.g., to be a spoof). In a similar manner, the coefficients may also be used for biometric verification by comparing the currently measured set of coefficients to a previously recorded set from a set of genuine measurements taken on a representative population of people.

Figure 12:
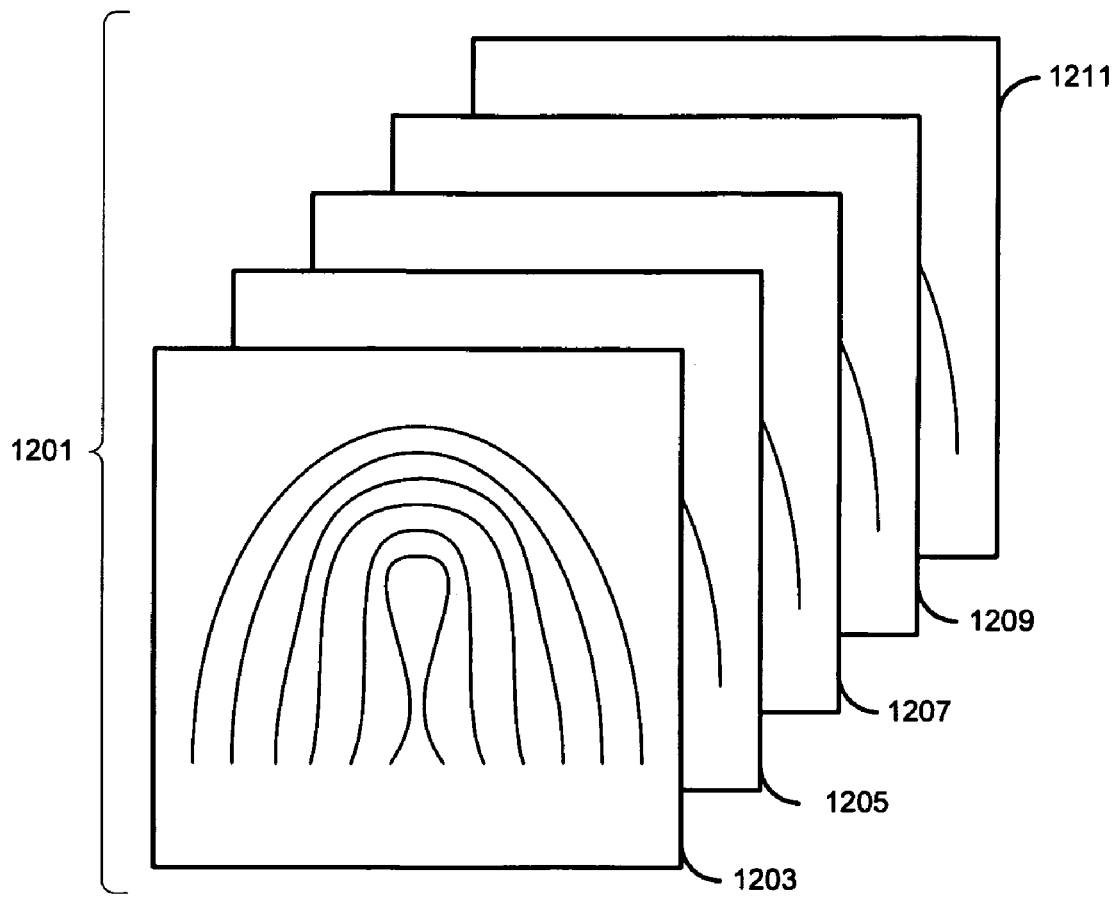
FIG. 12 shows an illustrative datacube form of storing or analyzing a body of spatio-spectral data.

Various embodiments described above may produce a body of spatio-spectral data, which may be used in various biometrics applications. The invention is not limited to any particular manner of storing or analyzing the body of spatio-spectral data. For purposes of illustration, it is shown in the form of a datacube in FIG. 12.

The datacube 1201 is shown decomposed along a spectral dimension with a plurality of planes 1203, 1205, 1207, 1209, 1211, each of which corresponds to a different portion of the light spectrum and each of which include spatial information. In some instances, the body of spatio-spectral data may include additional types of information beyond spatial and spectral information. For instance, different illumination conditions as defined by different illumination structures, different polarizations, and the like may provide additional dimensions of information.

In an embodiment where illumination takes place under white light, the images 1203, 1205, 1207, 1209, and 1211 might correspond, for example, to images generated using light at 450 nm, 500 nm, 550 nm, 600 nm, and 650 nm. In another example, there may be three images that correspond to the amount of light in the red, green, and blue spectral bands at each pixel location. Each image represents the optical effects of light of a particular wavelength interacting with skin. Due to the optical properties of skin and skin components that vary by wavelength, each of the multispectral images 1203, 1205, 1207, 1209, and 1211 will be, in general, different from the others. The datacube may thus be expressed as $R(X_S, Y_S, X_I, Y_I, \lambda)$ and describes the amount of diffusely reflected light of wavelength $\lambda$ seen at each image point $X_I, Y_I$ when illuminated at a source point $X_S, Y_S$. Different illumination configurations (flood, line, etc.) can be summarized by summing the point response over appropriate source point locations. A conventional non-TIR fingerprint image $F(X_I, Y_I)$ can loosely be described as the multispectral data cube for a given wavelength, $\lambda_o$, and summed over all source positions:

$$F(X_I, Y_I) = \sum_{Y_S} \sum_{X_S} R(X_S, Y_S, X_I, Y_I, \lambda_0).$$

Conversely, the spectral biometric dataset $S(\lambda)$ relates the measured light intensity for a given wavelength $\lambda$ to the difference $\vec{D}$ between the illumination and detection locations:

$$S(\vec{D},\lambda) = R(X_I - X_S, Y_I - Y_S, \lambda)$$

The datacube R is thus related to both conventional fingerprint images and to spectral biometric datasets. The datacube R is a superset of either of the other two data sets and contains correlations and other information that may be lost in either of the two separate modalities.

The light that passes into the skin and/or underlying tissue is generally affected by different optical properties of the skin and/or underlying tissue at different wavelengths. Two optical effects in the skin and/or underlying tissue that are affected differently at different wavelengths are scatter and absorbance. Optical scatter in skin tissue is generally a smooth and relatively slowly varying function wavelength. Conversely, absorbance in skin is generally a strong function of wavelength due to particular absorbance features of certain components present in the skin. For example blood, melanin, water, carotene, biliruben, ethanol, and glucose all have significant absorbance properties in the spectral region from 400 nm to 2.5 µm, which may sometimes be encompassed by the white-light sources.

The combined effect of optical absorbance and scatter causes different illumination wavelengths to penetrate the skin to different depths. This effectively causes the different spectral images to have different and complementary information corresponding to different volumes of illuminated tissue. In particular, the capillary layers close to the surface of the skin have distinct spatial characteristics that can be imaged at wavelengths where blood is strongly absorbing. Because of the complex wavelength-dependent properties of skin and underlying tissue, the set of spectral values corresponding to a given image location has spectral characteristics that are well-defined and distinct. These spectral characteristics may be used to classify the collected image on a pixel-by-pixel basis. This assessment may be performed by generating typical tissue spectral qualities from a set of qualified images. For example, the spatio-spectral data shown in FIG. 12 may be reordered as an N×5 matrix, where N is the number of image pixels that contain data from living tissue, rather than from a surrounding region of air. An eigen-analysis, Fisher linear discriminant analysis, or other factor analysis performed on this set matrix produces the representative spectral features of these tissue pixels. The spectra of pixels in a later data set may then be compared to such previously established spectral features using metrics such as Mahalanobis distance and spectral residuals. If more than a small number of image pixels have spectral qualities that are inconsistent with living tissue, then the sample is deemed to be non-genuine and rejected, thus providing a mechanism for incorporating anti-spoofing methods in the sensor based on determinations of the liveness of the sample.

The foregoing analysis framework can also be used to determine identity. In this case, the earlier reference data are taken from a single target individual rather than a representative user population. A subsequent successful comparison to a particular person's reference data may then establish both the identity and the genuineness of the measurement (e.g., assuming the earlier reference measurement is ensured to be genuine).

Alternatively, textural characteristics of the skin may alone or in conjunction with the spectral characteristics be used to determine the authenticity of the sample. For example, each spectral image may be analyzed in such a way that the magnitude of various spatial characteristics may be described. Methods for doing so include wavelet transforms, Fourier transforms, cosine transforms, gray-level co-occurrence, and the like. The resulting coefficients from any such transform described an aspect of the texture of the image from which they were derived. The set of such coefficients derived from a set of spectral images thus results in a description of the chromatic textural characteristics of the multispectral data. These characteristics may then be compared to similar characteristics of known samples to perform a biometric determination such as spoof or liveness determination. Alternatively, the characteristics may be compared to those developed from data taken on reputedly the same person at an earlier time to establish identity. Methods for performing such determinations are generally similar to the methods described for the spectral characteristics above. Applicable classification techniques for such determinations include linear and quadratic discriminant analysis, classification trees, neural networks, and other methods known to those familiar in the art.

Similarly, in an embodiment where the sample is a volar surface of a hand or finger, the image pixels may be classified as "ridge," "valley," or "other" based on their spectral qualities or their chromatic textural qualities. This classification can be performed using discriminant analysis methods such as linear discriminant analysis, quadratic discriminant analysis, principal component analysis, neural networks, and others known to those of skill in the art. Since ridge and valley pixels are contiguous on a typical volar surface, in some instances, data from the local neighborhood around the image pixel of interest are used to classify the image pixel. In this way, a conventional fingerprint image may be extracted for further processing and biometric assessment. The "other" category may indicate image pixels that have spectral qualities that are different than anticipated in a genuine sample. A threshold on the total number of pixels in an image classified as "other" may be set. If this threshold is exceeded, the sample may be determined to be non-genuine and appropriate indications made and actions taken.

In a similar way, multispectral data collected from regions such as the volar surface of fingers may be analyzed to directly estimate the locations of "minutiae points," which are defined as the locations at which ridges end, bifurcate, or undergo other such topographic change. For example, the chromatic textural qualities of the multispectral dataset may be determined in the manner described above. These qualities may then be used to classify each image location as "ridge ending," "ridge bifurcation," or "other" in the manner described previously. In this way, minutiae feature extraction may be accomplished directly from the multispectral data without having to perform computationally laborious calculations such as image normalization, image binarization, image thinning, and minutiae filtering, techniques that are known to those familiar in the art.

Biometric determinations of identity may be made using the entire body of spatio-spectral data or using particular portions thereof. For example, appropriate spatial filters may be applied to separate out the lower spatial frequency information that is typically representative of deeper spectrally active structures in the tissue. The fingerprint data may be extracted using similar spatial frequency separation and/or the pixel-classification methods disclosed above. The spectral information can be separated from the active portion of the image in the manner discussed above. These three portions of the body of spatio-spectral data may then be processed and compared to the corresponding enrollment data using methods known to one familiar in the art to determine the degree of match. Based upon the strength of match of these characteristics, a decision can be made regarding the match of the sample with the enrolled data. Additional details regarding certain types of spatio-spectral analyses that may be performed are provided in U.S. Pat. No. 7,147,153, entitled "MULTISPECTRAL BIOMETRIC SENSOR," filed Apr. 5, 2004 by Robert K. Rowe et al., the entire disclosure of which is incorporated herein by reference for all purposes.

It will now be appreciated that the various sensor embodiments may be used to detect locally consistent features of the skin site in a number of ways. Various embodiments may detect spatial, spectral, textural, and/or other information, alone or in combination, in series or in parallel. It will further be appreciated that many configurations of sensors may be used, according to the invention, some of which are described below.

Exemplary Application Embodiments

Small-area biometric sensors, such as those discussed above, may be embedded in a variety of systems and applications according to the invention. In some embodiments, the sensor is configured as a dedicated system that is connected to a PC or a network interface, an ATM, securing an entryway, or allowing access to a particular piece of electronics such as a cellular phone. In these embodiments, one or more people may be enrolled in the biometric system and use a particular reader to gain access to a particular function or area.

In other embodiments, the sensor is configured as a personal biometric system that confirms the identity of the sale person authorized to use the device, and transmits this authorization to any properly equipped PC, ATM, entryway, or piece of electronics that requires access authorization. In one embodiment, the personal biometric system transmits an identifying code to a requesting unit and then uses a biometric signal to confirm authorization. This may imply that the system needs to perform a verification task rather than a potentially more difficult identification task. Yet, from the user's perspective, the system may recognize the user without an explicit need to identify himself or herself. Thus, the system may appear to operate in an identification mode, which may be more convenient for the user.

An advantage of a personal biometric system may be that, if an unauthorized person is able to defeat the personal biometric system code for a particular biometric system-person combination, the personal biometric system may be reset or replaced to use a new identifying code and thus re-establish a secure biometric for the authorized person. This capability may be in contrast to multi-person biometric systems that base their authorization solely on a biometric signature (e.g., spatio-spectral information from a fingerprint). In this latter case, if an intruder is able to compromise the system by somehow imitating the signal from an authorized user, there may be no capability to change the biometric code when it is based solely on a fixed physiological characteristic of a person.

Figure 13:
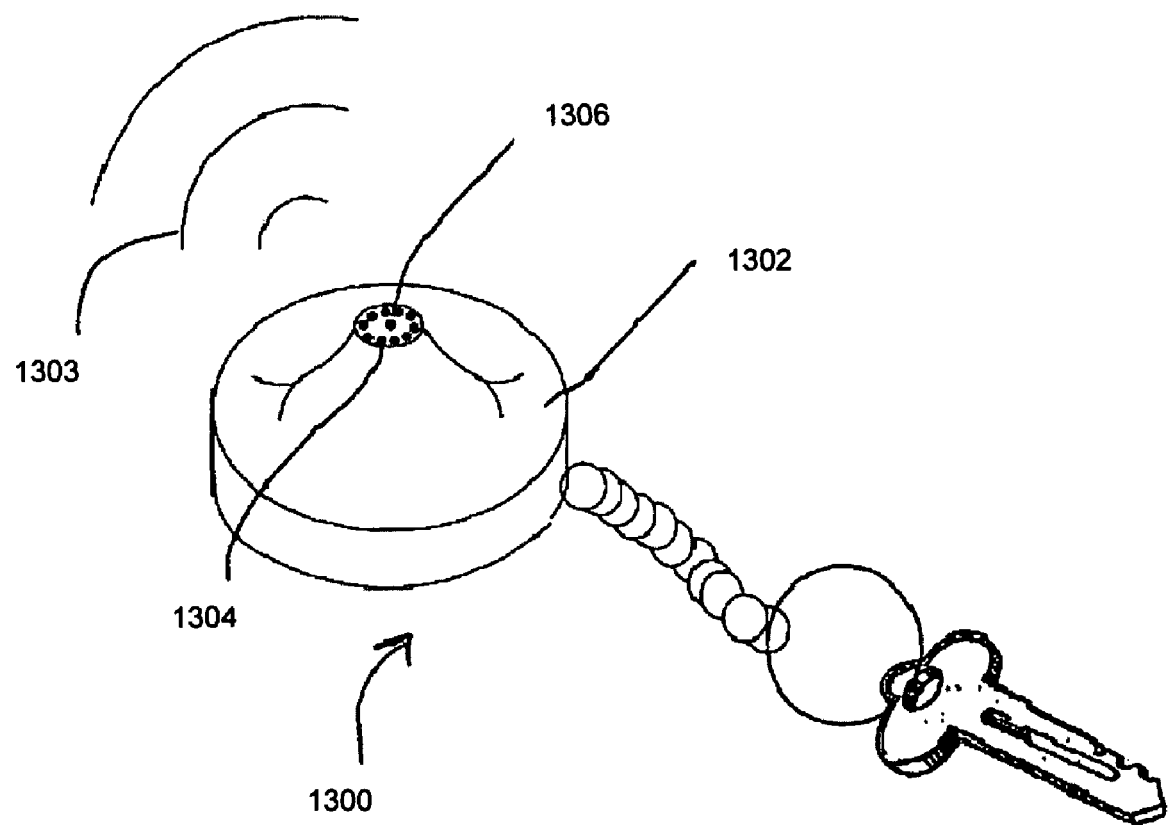
FIG. 13 shows an embodiment of a personal spectral biometric system in the configuration of an electronic key fob, according to various embodiments of the invention.

FIG. 13 shows one embodiment of a personal spectral biometric system 1300 in the configuration of an electronic key fob 1302. While an equidistant sensor configuration is shown, it will be appreciated that any type of sensor according to the invention may be used. In some embodiments, an illumination system 1304 and a detection system 1306 are built into the fob 1302, as is a means to collect and digitize the spectral information (not shown). In one embodiment, short-range wireless techniques 1303 (e.g., based upon RF signals) are transmitted to communicate between the fob and a corresponding reader (not shown), e.g., to allow access to a PC, entryway, etc. In another embodiment, an infrared optical signal is used to transmit information between the fob 1302 and the reader. In yet another embodiment, a direct electrical connection is established between the fob 1302 and the reader.

Actual processing of the detected biometric information may be made either within the fob 1302 or at the reader. In the former case, logical operations necessary to perform the comparison may be done within the fob 1302, and then a simple confirmation or denial signal may be transmitted to the reader. In the latter case, the detected biometric information may be transmitted from the fob 1302 to the reader (either all at once, serially, or in any other useful way), and the comparison and decision may be performed at the reader or at a host to which the reader is connected. In either case, the communication between the fob 1302 and the reader may be performed in a secure manner, e.g., to avoid interception and unauthorized use of the system. Methods for ensuring secure communication between two devices are well known to one of ordinary skill in the art.

Figure 14:
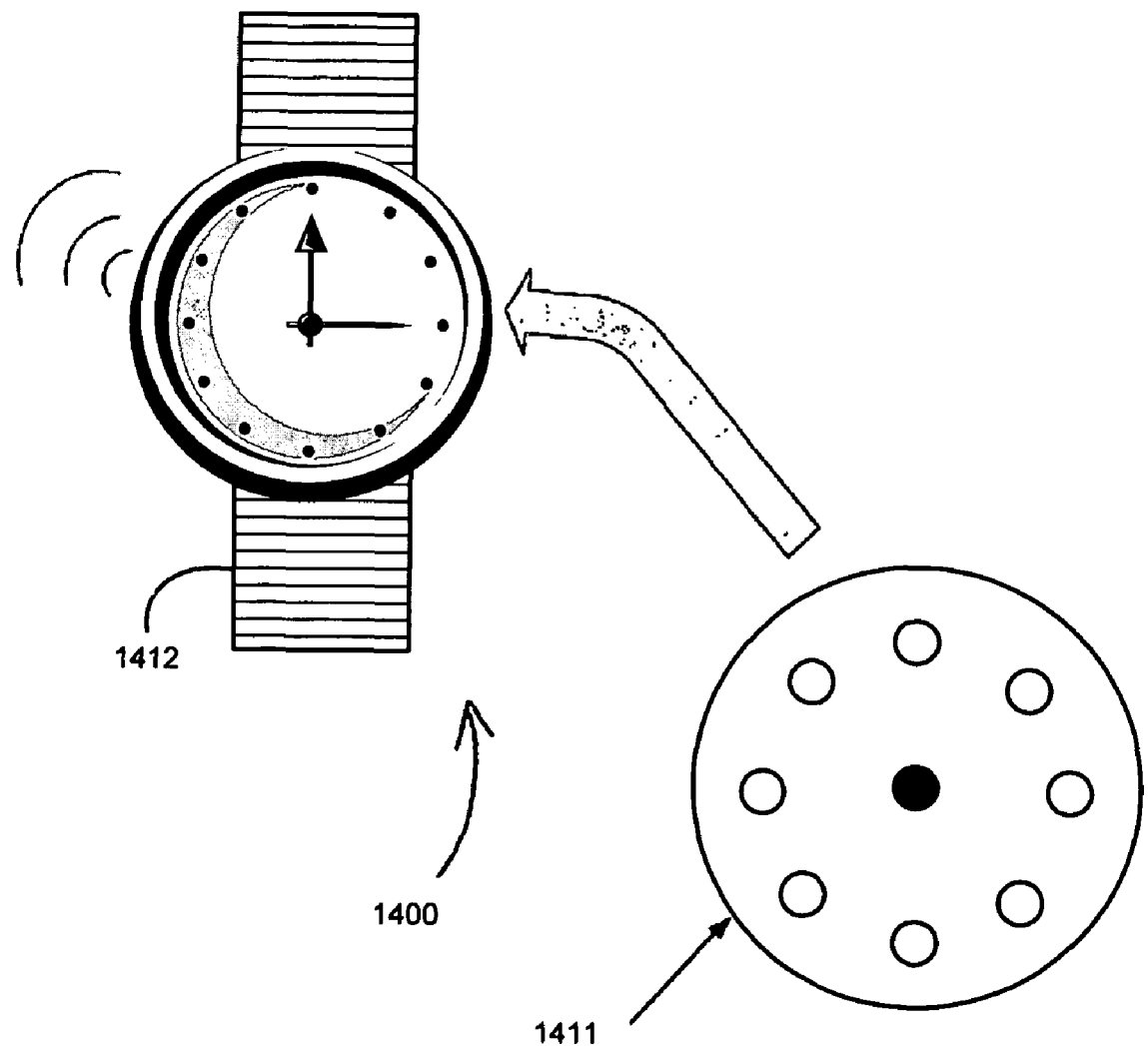
FIG. 14 shows an embodiment of a personal spectral biometric system in the configuration of a watch, according to various embodiments of the invention.

A second embodiment of a personal spectral biometric system 1400 is depicted in FIG. 14. In this embodiment, the biometric reader 1411 is built into the case of a watch 1412 and operates based upon signals detected from the skin proximate to the location of the watch (e.g., around the wrist). In certain embodiments, operation of this system may be identical to the operation described with respect to FIG. 13.

In addition to the watch or fob, similar biometric capability may be built into other personal electronic devices, including, for example, personal digital assistants ("PDAs") and cellular telephones. In each case, the personal biometric system may provide user authorization to access both the device in which it is installed, as well as authorization for mobile commerce ("M-Commerce") or other wireless transactions that the device may be capable of performing. Small-area sensors may also be put into firearms, commercial equipment, power tools, or other potentially dangerous devices or systems, e.g., to prevent unauthorized or unintended usage. For example, a biometric sensor may be placed in the handgrip of a firearm to sense tissue properties while the gun is being held in a normal manner.

Further embodiments provide the ability to identify people who are to be explicitly excluded from accessing protected property as well as determining those who are authorized to access the property. This capability may, for example, improve the biometric performance of the system with respect to those unauthorized people who are known to attempt to use the device, which could be particularly important in certain cases (e.g., the case of a personal handgun). In particular, parents who own a biometrically enabled handgun may enroll themselves as authorized users and also can enroll their children as explicitly unauthorized users. In this way, parents may have further insurance that children who are known to be in the same household as a gun will not be able to use it.

Even further embodiments use the explicit-denial capability of a biometric system in a fixed installation such as a home, place of business, or an automobile. For example, a biometric system installed at the-entryway of a place of business can be used to admit authorized employees and temporary workers. If an employee is fired or the term of the temporary employee expires, then their enrollment data can be shifted from the authorized to the unauthorized database, and an explicit check is made to deny access to the former employee if he or she attempts to enter.

It will be appreciated that the applications described herein are only examples, and that many other applications may be possible. For example, many spatio-spectral features may be indicative of living tissue, allowing some sensors to be used to detect the "liveness" of a sample. This may deter certain types of circumvention attempts, like the use of latex or wax "surrogates," or dead or excised tissue. In some applications, such as Internet access authorization, it may be useful to be able to verify the sex and/or age of the person using the spectral biometric system. Because ages and sexes may manifest in different ways in skin structure and composition, the optical spectra may also change in systematic and indicative ways, such that age and sex may be estimated using the biometric data. Additional details regarding estimation of certain personal characteristics from biometric measurements are provided in U.S. Pat. No. 7,623,313, entitled "METHODS AND SYSTEMS FOR ESTIMATION OF PERSONAL CHARACTERISTICS FROM BIOMETRIC MEASUREMENTS," filed Dec. 9, 2004 by Robert K. Rowe, the entire disclosure of which is incorporated herein by reference for all purposes.

Figure 15:
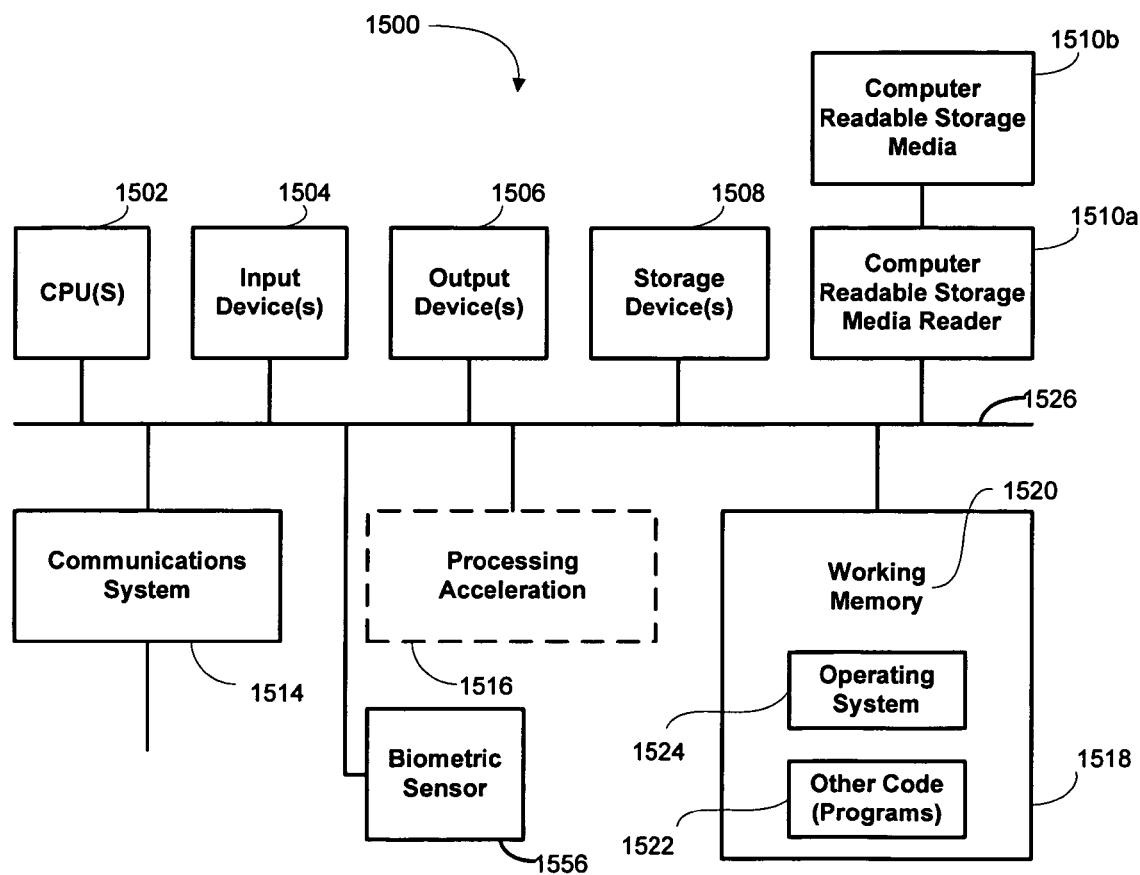
FIG. 15 shows an exemplary computational system for implementing biometric sensors and related functionality according to various embodiments of the invention.

In various embodiments, a biometric sensor of any of the types described above may be operated by a computational system to implement biometric functionality. FIG. 15 broadly illustrates how individual system elements may be implemented in a separated or more integrated manner. The computational device 1500 is shown comprised of hardware elements that are electrically coupled via bus 1526, which is also coupled with the biometric sensor 1556. The hardware elements include a processor 1502, an input device 1504, an output device 1506, a storage device 1508, a computer-readable storage media reader 1510*a*, a communications system 1514, a processing acceleration unit 1516 such as a DSP or special-purpose processor, and a memory 1518. The computer-readable storage media reader 1510*a* is further connected to a computer-readable storage medium 1510*b*, the combination comprehensively representing remote, local, fixed, and/or removable storage devices plus storage media for temporarily and/or more permanently containing computer-readable information. The communications system 1514 may comprise a wired, wireless, modem, and/or other type of interfacing connection and permits data to be exchanged with external devices.

The computational device 1500 also comprises software elements, shown as being currently located within working memory 1520, including an operating system 1524 and other code 1522, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

It will be appreciated that these units of the device may, individually or collectively, be implemented with one or more Application Specific Integrated Circuits (ASICs) adapted to perform some or all of the applicable functions in hardware. Alternatively, the functions may be performed by one or more other processing units (or cores), on one or more integrated circuits. In other embodiments, other types of integrated circuits may be used (e.g., Structured/Platform ASICs, Field Programmable Gate Arrays (FPGAs), and other Semi-Custom ICs), which may be programmed in any manner known in the art. The functions of each unit may also be implemented, in whole or in part, with instructions embodied in a memory, formatted to be executed by one or more general or application-specific processors.

Exemplary Methods

Figure 16:
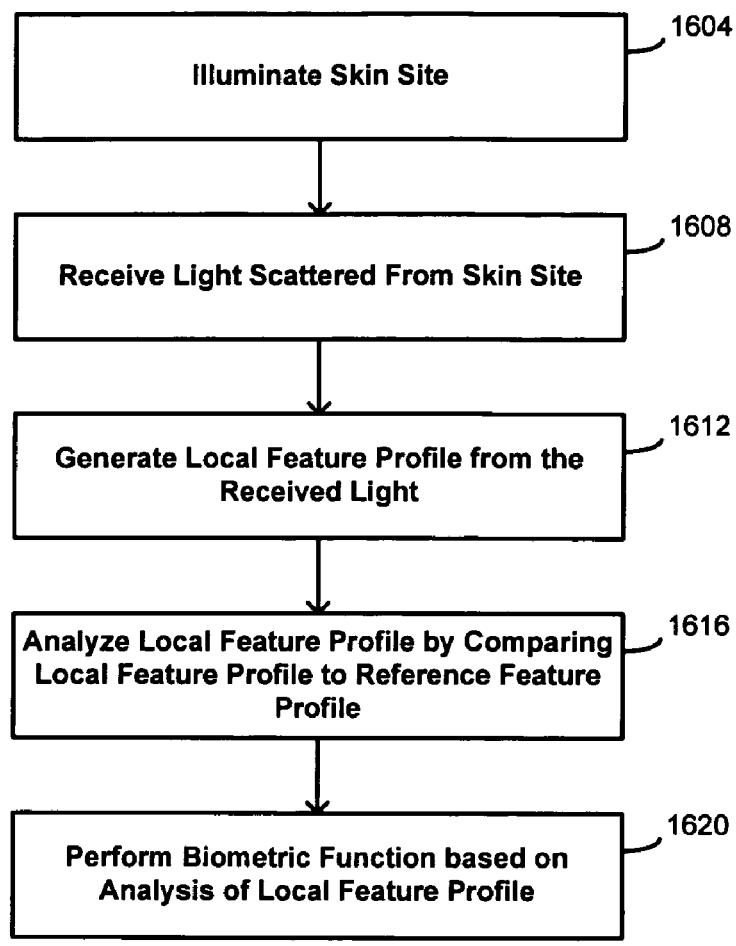
FIG. 16 provides a flow diagram of exemplary methods for using multispectral sensor structures according to various embodiments of the invention.

FIG. 16 provides a flow diagram of exemplary methods for using multispectral sensor structures according to embodiments of the invention. While the drawing shows a number of steps performed in a particular order, this is intended to be illustrative rather than limiting. In other embodiments, the steps may be performed in a different order, further steps may be added, and/or some steps identified specifically may be omitted.

At block 1604, a skin site of an individual is illuminated. In some embodiments, the skin site is illuminated under a plurality of distinct optical conditions, e.g., including a plurality of wavelengths, polarizations, and/or source-detector spacings. Light scattered from the skin site is received at block 1608. An image is then formed of the skin site from the received light (e.g., by generating images of the skin site corresponding to the distinct optical conditions) to generate a local feature profile at block 1612. The local feature profile may characterize a locally consistent feature of the skin site being imaged.

At block 1616, the local feature profile may be analyzed. In some embodiments, this analysis includes comparing the local feature profile to a reference feature profile. In certain embodiments, the reference feature profile includes image data relating to locally consistent features of the individual using the sensor. For example, the data may come from previous uses of the sensor and/or from a database of previously collected images. Further, in some embodiments, the sensor may be capable of "learning" over time by enhancing its analysis algorithm. For example, genetic algorithms, image averaging, neural networks, and other techniques may be used.

Based on the analysis of the local feature profile, a biometric function may be performed at block 1620. In some embodiments, the biometric function comprises an identity function. For example, the local feature profile may be compared with stored reference feature profiles to identify the individual or to confirm the identity of the individual. In other embodiments, the biometric function includes demographic, anthropomorphic, liveness, analyte measurement, and/or other biometric functions.

This description provides example embodiments only, and is not intended to limit the scope, applicability or configuration of the invention. Rather, the ensuing description of the embodiments will provide those skilled in the art with an enabling description for implementing embodiments of the invention. Various changes may be made in the function and arrangement of elements without departing from the spirit and scope of the invention. Also, it should be emphasized that technology evolves and, thus, many of the elements are examples and should not be interpreted to limit the scope of the invention.

Thus, various embodiments may omit, substitute, or add various procedures or components as appropriate. For instance, it should be appreciated that in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Moreover, as disclosed herein, the term "memory" or "memory unit" may represent one or more devices for storing data, including read-only memory (ROM), random access memory (RAM), magnetic RAM, core memory, magnetic disk storage mediums, optical storage mediums, flash memory devices, or other computer-readable mediums for storing information. The term "computer-readable medium" includes, but is not limited to, portable or fixed storage devices, optical storage devices, wireless channels, a sim card, other smart cards, and various other mediums capable of storing, containing, or carrying instructions or data.

Furthermore, embodiments may be implemented by hardware, software, firmware, middleware, microcode, hardware description languages, or any combination thereof. When implemented in software, firmware, middleware, or microcode, the program code or code segments to perform the necessary tasks may be stored in a computer-readable medium such as a storage medium. Processors may perform the necessary tasks.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention, which is defined in the following claims.

What is claimed is:

1. A method of performing a biometric identification, the method comprising:
    illuminating a small-area of a finger of an individual with illumination light from an illumination source;
    receiving, at a sensor, light scattered from the small-area of the finger;
    generating, with a processor, a local feature profile from the received light, wherein the local feature profile identifies a feature of the small-area of the finger, the feature of the small-area of the finger being of a type predetermined to exhibit substantial local consistency; and
    analyzing, with a processor, the generated local feature profile to perform the biometric identification,
    wherein analyzing the generated local feature profile comprises comparing the generated local feature profile with a reference local feature profile,
    wherein the reference local feature profile was generated from light scattered from a small-area reference skin site, and
    wherein the small-area of the finger is from a substantially different portion of the finger than the small-area reference skin site.

2. The method recited in claim 1, wherein the small-area of the finger is in contact with a surface.

3. The method recited in claim 2, wherein the light is received substantially in a plane that includes the surface.

4. The method recited in claim 1, wherein the small-area of the finger is a volar skin surface of the individual.

5. The method recited in claim 4, wherein the volar skin surface of the individual comprises a portion of a fingerprint of the individual.

6. The method recited in claim 1, wherein generating the local feature profile comprises:
    forming an image from the received light;
    generating spatially-distributed multispectral data from the image; and
    processing the spatially-distributed multispectral data to generate the local feature profile.

7. The method recited in claim 1, wherein generating the local feature profile comprises:
    forming an image from the received light;
    generating an image-texture measure from the image; and
    processing the generated image-texture measure to generate the local feature profile.

8. The method recited in claim 1 wherein:
    the biometric function comprises an antispoofing function; and
    analyzing the generated local feature profile comprises determining whether the small-area of the finger comprises living tissue from the generated local feature profile.

9. The method recited in claim 1 wherein:
the biometric function comprises an identity function; and
analyzing the generated local feature profile comprises determining an identity of the individual from the generated local feature profile.

10. The method recited in claim 1 wherein:
the biometric function comprises a demographic function; and
analyzing the generated local feature profile comprises estimating a demographic characteristic of the individual from the generated local feature profile.

11. The method recited in claim 1 wherein:
the biometric function comprises an anthropometric function; and
analyzing the generated local feature profile comprises estimating an anthropometric characteristic of the individual from the generated local feature profile.

12. The method recited in claim 1 wherein:
receiving light scattered from the small-area of the finger comprises receiving light scattered from the small-area of the finger at an imaging detector.

13. The method recited in claim 12 wherein:
receiving light scattered from the small-area of the finger comprises receiving light scattered from the small-area of the finger at a surface plane of the imaging detector.

14. The method recited in claim 12 wherein receiving light scattered from the small-area of the finger comprises:
receiving a pattern of light at a surface plane of a sensor platen;
translating the pattern of light from the surface plane of the platen to the imaging detector without substantial degradation or attenuation of the pattern of light, wherein the imaging detector is disposed outside the surface plane of the platen; and
receiving the translated pattern of light at the imaging detector.

15. The method recited in claim 1 wherein the illumination light is white light.

16. The method recited in claim 1 wherein illuminating the small-area of the finger comprises illuminating the small-area of the finger under a plurality of distinct optical conditions.

17. The method recited in claim 16 wherein illuminating the small-area of the finger under the plurality of distinct optical conditions comprises illuminating the small-area of the finger with light under a plurality of distinct polarization conditions.

18. The method recited in claim 16 wherein illuminating the small-area of the finger under the plurality of distinct optical conditions comprises illuminating the small-area of the finger with white light under a plurality of distinct wavelengths.

19. The method recited in claim 16 wherein generating the local feature profile from the received light comprises:
generating a plurality of images, each of the plurality of images corresponding to one of the distinct optical conditions; and
applying a compositing algorithm to the plurality of images.

20. The method recited in claim 16 wherein the reference local feature profile was further generated by:
generating a composite reference image from a plurality of images, each of the plurality of images corresponding to a previously imaged small-area reference skin site.

21. The method recited in claim 16 wherein illuminating the small-area of the finger under the plurality of distinct optical conditions comprises illuminating the small-area of the finger with light having a plurality of different wavelengths.

22. The method recited in claim 21 wherein generating the local feature profile comprises:
generating a plurality of images corresponding to the different wavelengths; and
performing a spatial moving-window analysis of at least a portion of the plurality of images.

23. The method recited in claim 22 wherein performing the spatial moving-window analysis comprises calculating a moving-window Fourier transform on the plurality of images.

24. The method recited in claim 22 wherein performing the spatial moving-window analysis comprises calculating a moving-window centrality measure and a moving-window variability measure of the plurality of images.

25. The method recited in claim 1 wherein receiving light scattered from the small-area of the finger comprises receiving light scattered from the small-area of the finger at a monochromatic imaging detector.

26. The method recited in claim 1 wherein receiving light scattered from the small-area of the finger comprises receiving light scattered from the small-area of the finger at a color imaging detector.

27. The method recited in claim 1 further comprising:
comparing spectral features of the received light with reference spectral features in performing the biometric function.

28. A biometric sensor comprising:
an illumination subsystem disposed to illuminate a small-area of a finger of an individual with illumination light;
a detection subsystem disposed to receive light scattered from the small-area of the finger; and
a computational unit interfaced with the detection subsystem and having:
instructions for generating a local feature profile from the received light, wherein the local feature profile identifies a feature of the small-area of the finger, the feature of the small-area of the finger being of a type predetermined to exhibit substantial local consistency; and
instructions for analyzing the generated local feature profile to perform a biometric identification,
wherein analyzing the generated local feature profile comprises comparing the generated local feature profile with a reference local feature profile,
wherein the reference local feature profile was generated from light scattered from a small-area reference skin site, and
wherein the small-area of the finger is from a substantially different portion of the finger than the reference small-area skin site.

29. The biometric sensor recited in claim 28, further comprising:
a surface disposed for contact with the small-area of the finger of the individual.

30. The biometric sensor recited in claim 29, wherein:
the illumination subsystem is disposed to illuminate the small-area of the finger when the small-area of the finger is in contact with the surface.

31. The biometric sensor recited in claim 29, wherein:
the light is received substantially in a plane that includes the surface.

32. The biometric sensor recited in claim 28, wherein the small-area of the finger is a volar skin surface of the individual.

33. The biometric sensor recited in claim 32, wherein the volar skin surface of the individual comprises a portion of a fingerprint of the individual.

34. The biometric sensor recited in claim 28, wherein the instructions for generating the local feature profile comprise:
- forming an image from the received light;
- generating spatially-distributed multispectral data from the image; and
- processing the spatially-distributed multispectral data to generate the local feature profile.

35. The biometric sensor recited in claim 28, wherein the instructions for generating the local feature profile comprise:
- forming an image from the received light;
- generating an image-texture measure from the image; and
- processing the generated image-texture measure to generate the local feature profile.

36. The biometric sensor recited in claim 28 wherein:
- the biometric function comprises an antispoofing function; and
- the instructions for generating the local feature profile comprise determining whether the small-area of the finger comprises living tissue from the generated local feature profile.

37. The biometric sensor recited in claim 28 wherein:
- the biometric function comprises an identity function; and
- the instructions for generating the local feature profile comprise determining an identity of the individual from the generated local feature profile.

38. The biometric sensor recited in claim 28 wherein:
- the biometric function comprises a demographic function; and
- the instructions for generating the local feature profile comprise estimating a demographic characteristic of the individual from the generated local feature profile.

39. The biometric sensor recited in claim 28 wherein:
- the biometric function comprises an anthropometric function; and
- the instructions for generating the local feature profile comprise estimating an anthropometric characteristic of the individual from the generated local feature profile.

40. The biometric sensor recited in claim 28 further comprising an imaging detector, wherein:
- the detection subsystem comprises the imaging detector and is configured to receive light scattered from the small-area of the finger at the imaging detector.

41. The biometric sensor recited in claim 40 wherein:
- the detection subsystem is configured to receive light scattered from the small-area of the finger at a surface plane of the imaging detector.

42. The biometric sensor recited in claim 40 further comprising:
- a sensor platen comprising a surface plane;
- an imaging detector disposed outside the surface plane of the sensor platen; and
- an optical arrangement configured to translate a pattern of light from the surface plane of the sensor platen to the imaging detector without substantial degradation or attenuation of the pattern of light,
- wherein the detection subsystem comprises the imaging detector and is configured to receive the translated pattern of light at the imaging detector.

43. The biometric sensor recited in claim 40 wherein:
- the imaging detector is a monochromatic imaging detector.

44. The biometric sensor recited in claim 40 wherein:
- the imaging detector is a color imaging detector.

45. The biometric sensor recited in claim 28 wherein the illumination light is white light.

46. The biometric sensor recited in claim 28 wherein the illumination subsystem is disposed to illuminate the small-area of the finger under a plurality of distinct optical conditions.

47. The biometric sensor recited in claim 46 wherein the plurality of distinct optical conditions comprises a plurality of distinct polarization conditions.

48. The biometric sensor recited in claim 46 wherein the plurality of distinct optical conditions comprises white light under a plurality of distinct wavelengths.

49. The biometric sensor recited in claim 46 wherein the instructions for generating the local feature profile from the received light comprise:
- instructions for generating a plurality of images, each of the plurality of images corresponding to one of the distinct optical conditions; and
- instructions for applying a compositing algorithm to the plurality of images.

50. The biometric sensor recited in claim 46 wherein the reference local feature profile was further generated by:
- generating a composite reference image from a plurality of images, each of the plurality of images corresponding to a previously imaged small-area reference skin site.

51. The biometric sensor recited in claim 46 wherein the plurality of distinct optical conditions comprises light having a plurality of different wavelengths.

52. The biometric sensor recited in claim 51 wherein the instructions for generating the local feature profile comprise:
- instructions for generating a plurality of images corresponding to the different wavelengths; and
- instructions for performing a spatial moving-window analysis of at least a portion of the plurality of images.

53. The biometric sensor recited in claim 52 wherein the instructions for performing the spatial moving-window analysis comprise calculating a moving-window Fourier transform on the plurality of images.

54. The biometric sensor recited in claim 52 wherein the instructions for performing the spatial moving-window analysis comprise calculating a moving-window centrality measure and a moving-window variability measure of the plurality of images.

55. The biometric sensor recited in claim 28 wherein the computational unit further has instructions for comparing spectral features of the received light with reference spectral features in performing the biometric function.

56. The biometric sensor recited in claim 28 wherein an exposed surface of the sensor has an area less than 0.75 cm2.

57. The biometric sensor recited in claim 28 wherein an exposed surface of the sensor has an area less than 0.5 cm2.

58. The biometric sensor recited in claim 28 wherein an exposed surface of the sensor has an area less than 0.25 cm2.

59. The biometric sensor recited in claim 28 wherein an exposed surface of the sensor has an area less than 0.1 cm2.

60. The biometric sensor recited in claim 28 wherein an exposed surface of the sensor has an area less than 0.05 cm2.

61. The biometric sensor recited in claim 28 wherein an exposed surface of the sensor has an area less than 0.01 cm2.

62. The biometric sensor recited in claim 28 wherein the sensor is substantially a point sensor.

* * * * *